United States Patent [19]
Vogt

[11] 4,213,982
[45] Jul. 22, 1980

[54] NOVEL 4H-s-TRIAZOLO[4,3-a][1,5]BENZODIAZEPIN-5-ONES

[75] Inventor: B. Richard Vogt, Yardley, Pa.

[73] Assignee: E. R. Squibb & Sons, Inc., Princeton, N.J.

[21] Appl. No.: 944,532

[22] Filed: Sep. 21, 1978

Related U.S. Application Data

[62] Division of Ser. No. 778,823, Mar. 17, 1977, Pat. No. 4,133,809, which is a division of Ser. No. 365,012, May 29, 1973, abandoned.

[51] Int. Cl.$^2$ .................. A61K 31/535; A61K 31/41; A61K 31/44; A61K 445
[52] U.S. Cl. ............... 424/248.52; 424/248.4; 424/248.5; 424/248.54; 424/248.57; 424/263; 424/267; 424/269; 424/272
[58] Field of Search .......... 424/269, 267, 263, 272; 424/248.5, 248.52, 248.54, 248.57, 248.4

[56] References Cited

U.S. PATENT DOCUMENTS

Re. 28,505  8/1975  Hester .................. 424/267
4,075,202  2/1978  Moffett ................ 424/244

Primary Examiner—Frederick E. Waddell
Attorney, Agent, or Firm—Lawrence S. Levinson; Burton Rodney

[57] ABSTRACT

Compounds of the following formula

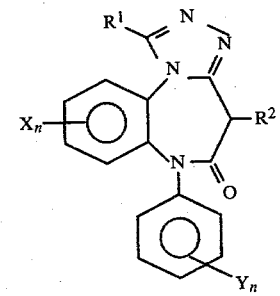

are useful as central nervous system depressants, tranquilizers, sedatives, growth promotors, anti-convulsants and muscle relaxants in mammalian species.

7 Claims, No Drawings

NOVEL 4H-S-TRIAZOLO[4,3-A][1,5]BENZODIAZEPIN-5-ONES

RELATED APPLICATION

This is a division of application Ser. No. 778,823, filed Mar. 17, 1977, now U.S. Pat. 4,133,809 which is a division of application Ser. No. 365,012 as filed May 29, 1973, now abandoned.

OBJECTS OF THE INVENTION

It is an object of the present invention to provide new compounds which are useful as central nervous system depressants, tranquilizers and sedatives. Another object is to provide methods for the preparation of these compounds. Another object is to provide compositions for the administration of the compounds of the invention. These and other objects of the present invention will be apparent from the following description.

SUMMARY OF THE INVENTION

It has now been found that 4H-s-triazolo[4,3-a]-[1,5]benzodiazepin-5-ones of the following formula

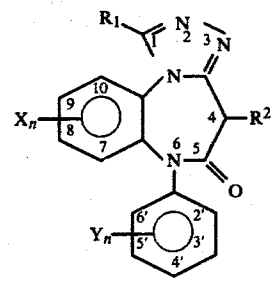

are useful CNS depressants, tranquilizers, sedatives, growth promotors, anti-convulsants and muscle relaxants in mammalian species.

DETAILED DESCRIPTION

The novel 4H-s-triazolo[4,3-a][1,5]benzodiazepin-5-ones of formula 1 are useful CNS depressants, tranquilizers and sedatives. The novel compounds of formulas 3–12, and the compounds of formulas 13 and 14 some of which are also novel, are intermediates for the compounds of formula 1.

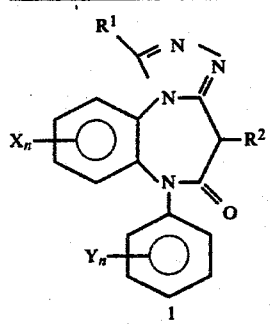

1

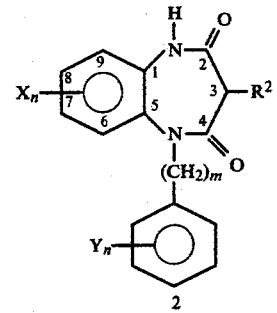

2

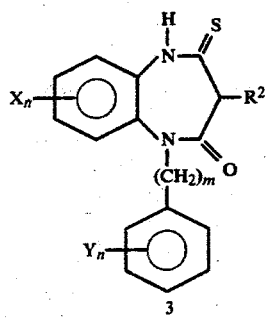

3

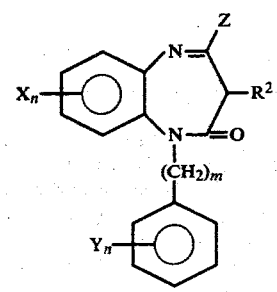

4. $Z = SR^3$
5. $Z = $ halogen
6. $Z = OR^3$
7. $Z = NHNHCR^1$ (with =O on C)
8. $Z = NHNH_2$
9. $Z = NHNHCOR^4$ -continued

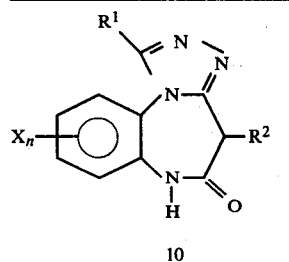

10

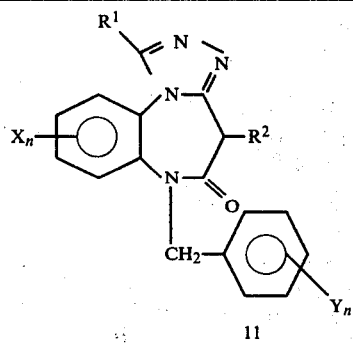

11

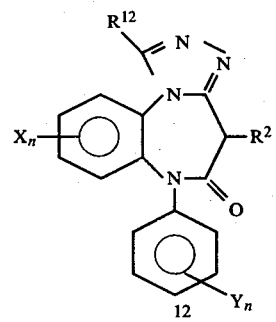

12

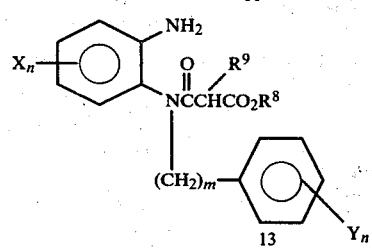

13

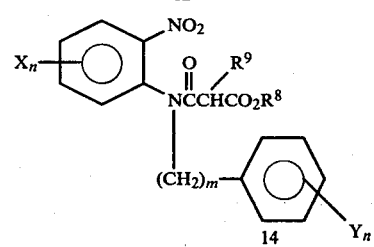

14

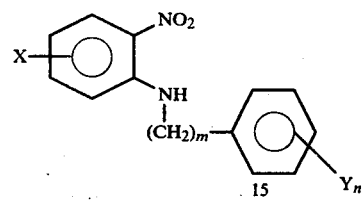

15

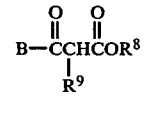

16

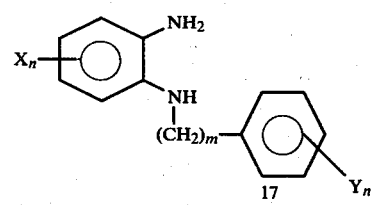

17

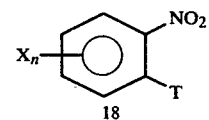

18

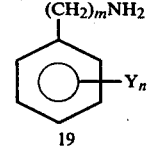

19

In the foregoing formulas $R^1$ is H; phenyl; X-substituted phenyl wherein X is as defined below; 2-, 3- or 4-pyridyl, cycloalkyl of 3-5 carbons, alkyl of 1-4 carbons optionally substituted by amino, by monoalkylamino of 1-4 carbons, by dialkylamino of 1-4 carbons, by nitro, by cyano, by hydroxy, by alkoxy of 1-4 carbons, by alkanoyloxy of 1-4 carbons, by phenyl wherein the phenyl ring is optionally substituted by one or more X groups wherein X is as defined below, or by a cyclic imine of formula

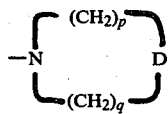

where D is methylene, oxygen or $N-R^{10}$ and where p and q may be the same or different and are the integers 1, 2, and 3 provided that p+q is at least 1;

$R^2$ is H; alkyl of 1-4 carbons optionally substituted by amino, mono-lower alkyl, di-lower alkyl amino, cyclic imines of formula

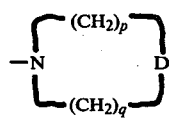

where the cyclic imine is as defined above; hydroxy; alkoxy of 1-6 carbons or

where

is an acyl group capable of removal and replacement by hydrogen or alkyl of 1–4 carbons and $R^5$ is alkyl of 1–5 carbons optionally substituted by phenyl or X-substituted phenyl; or $R^5$ is phenyl optionally substituted by 1 or more X-substituents X and Y can be the same or different and are hydrogen, F, Cl, Br, trifluomethyl, alkyl of from 1–6 carbons, alkoxy of from 1–6 carbons, nitro, cyano, amino, alkanoylamino of 1–4 carbons, alkylthio of 1–6 carbons, alkylsulfinyl of 1–6 carbons or alkyl sulfonyl of 1–6 carbons;

$R^3$ is alkyl of from 1–6 carbons, benzyl or phenethyl;

$R^4$ is t-butyl or benzyl optionally substituted on the phenyl ring by one to three X groups;

$R^8$ is alkyl of from 1–6 carbons, or phenyl optionally substituted by any alkyl, aralkyl or aryl radical compatible with cyclization to form a 7-membered ring;

$R^9$ is hydrogen or alkyl of from 1–4 carbons;

n is 0, 1 or 2; m is 0 or 1;

$R^{10}$ is hydrogen, alkyl of 1–4 carbons or phenyl optionally substituted by X;

T is halogen, preferably chlorine, bromine or iodine.

$R^{11}$ is hydrogen or alkyl of 1–4 carbons;

$R^{12}$ is alkyl of 1–4 carbons substituted by the groups

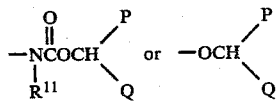

where P and Q may be the same or different and may be hydrogen, phenyl, X-substituted phenyl, naphthyl or X-substituted naphthyl, with the proviso that at least one of P and Q is one of the foregoing aryl radicals, $R^{13}$ is alkyl of 1–6 carbons.

Preferably, $R^1$ is hydrogen, cycloalkyl of 3–5 carbons, or alkyl of 1–4 carbons optionally substituted by amino, nitro, cyano, hydroxy, alkoxy of 1–4 carbons, alkanoyloxy of 1–4 carbons, mono-alkylamino of 1–4 carbons, dialkylamino of 1–4 carbons or by a cyclic imine of formula

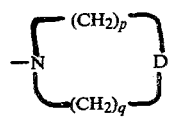

where D, p and q are as previously defined. Most preferably, $R^1$ is hydrogen or alkyl of 1–4 carbons.

Preferably, $R^2$ is hydrogen, alkyl of 1–4 carbons or hydroxy.

Preferably, $R^8$ is alkyl of 1–4 carbons. The radical $R^8$ as well as the oxygen atom to which it is bonded are removed during cyclization.

SYNTHESIS

The 4-H-s-triazolo[4,3-a][1,5]benzodiazepin-5-ones of formulas 1 and 11 can be prepared by several methods.

One method (hereinafter called the first method) involves reacting a compound of formulas 3–6 with from about 0.8 to about 6.0, preferably from about 1.0 to about 3.0 molar equivalents of an acid hydrazide of formula

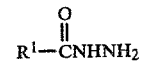

(where $R^1$ is as defined previously) in an inert, organic solvent or mixture of solvents. Typical organic solvents which may be used in the above reaction include aryl hydrocarbons, e.g., benzene, toluene, xylene and the like; chlorinated hydrocarbons such as di-, tri-, tetra-chloroethanes and the like; lower molecular weight alkanols of 1–6 carbons such as methanol, ethanol, tertiary butyl alcohol, n-butanol and the like; N,N-dialkyl-formamides, N,N-dialkyl alkanoyl amides wherein the alkyl and alkanoyl radicals have 1–4 carbons, such as dimethylformamide, dimethylacetamide and the like; hexamethylphosphorous triamide, ethers, such as dioxane and the like and di-lower alkyl sulfoxides, such as dimethyl sulfoxide and the like. The reaction is carried out at from about 40° C. to about 250° C., preferably from about 60° C. to about 180° C., until a significant amount of end product is obtained, typically, for from about ¼ to about 92 hours, preferably from about 1 to about 48 hours.

The final product of formula 1 or 11 is isolated by conventional techniques. For example, the reaction mixture is evaporated and the residue is partitioned between aqueous sodium bicarbonate and a water-immiscible inert, organic solvent, such as halogenated hydrocarbons, e.g., methylene chloride, chloroform or trichloroethylene; alkyl esters wherein both the acid and alcohol from which the ester is derived may have from 1 to 4 carbon atoms, e.g., ethyl acetate, propyl acetate, ethyl propionate and the like. The organic solvent is washed with water, dried and chromatographed.

A compound of formula 12 may be converted to the corresponding compound of formula 1 by another method for the synthesis of compounds of formula 1 where $R^1$ is alkyl substituted by amino, mono-alkyl amino or a hydroxy group. Such a method involves reacting a compound of formula 12 with appropriate reagents under appropriate conditions as described below suitable for the selective replacement of the

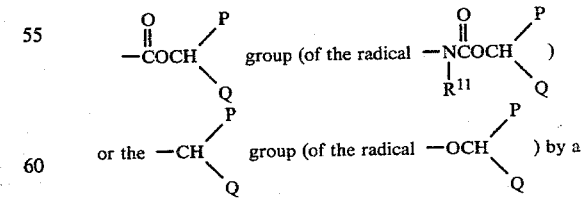

hydrogen atom.

One such method involves reacting the compounds of formula 12 with at least about 0.5 preferably at least about 0.8, molar equivalent of an inorganic hydrogen halide (preferably hydrogen chloride, hydrogen bromide and hydrogen fluoride) or with a halogenated lower alkyl carboxylic acid (preferably trifluoroacetic acid). The reaction is run in anhydrous hydrogen fluoride, or, when employing other acids, in an optional inert solvent.

Typical solvents include lower carboxylic acid such as acetic acid and the like; ethers such as diethyl ether, dioxane, tetrahydrofuran and the like; lower molecular weight alkanols of 1-6 carbons such as methanol, ethanol, and the like; alkyl esters wherein both the acid and the alcohol from which the ester is derived may have from 1-4 carbon atoms such as ethyl acetate, propyl acetate, ethyl propionate and the like; halogenated hydrocarbons such as methylene chloride, chloroform, di-, tri- and tetrachloroethanes and the like; nitroalkanes of 1-4 carbons such as nitromethane, nitroethane and the like; or lower alkyl ketones of 2-5 carbons such as acetone, methylethyl ketone and the like.

The reaction is carried out at from about −50° C. to about 200° C., preferably from about 0° C. to about 120° C., until a significant amount of end product is obtained, typically, for from about 1/10 to about 92, preferably from about 1/6 to about 30 hours. The corresponding product of formula 1 is isolated by conventional techniques. For example, with all acids except hydrogen fluoride, the reaction mixture is diluted with an inert water-immiscible organic solvent, washed with dilute aqueous sodium bicarbonate, dried and chromatographed. When using hydrogen fluoride, the hydrogen fluoride is evaporated, the residue dissolved in an inert organic solvent, such as halogenated hydrocarbons such as, e.g., methylene chloride, chloroform or trichloroethylene; alkyl esters wherein both the acid and the alcohol from which the ester is derived may have from 1-4 carbon atoms, e.g., ethylacetate, propyl acetate, ethyl propionate and the like, washed with water, dried and chromatographed.

Another such method for the selective replacement of the

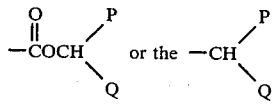

group by hydrogen in compounds of formula 12 involves the reaction of said compounds of formula 12 with hydrogen in the presence of an appropriate catalyst, in an inert organic solvent. Typical catalysts include platinum, Raney nickel and, preferably, palladium. Typical solvents include lower alkanols of 1-6 carbons such as ethanol, methanol, and the like; formic acid; lower alkanoic acids of 2-5 carbons such as acetic acid and the like as well as other typical solvents well known to those versed in the art. Typical hydrogenation pressures are from about 0.1 to about 2000 atmospheres, preferably from about 0.8 to about 100 atmospheres. The reactions are carried out for from about ½ to about 96 hours, preferably from about 1 to about 72 hours at from about 0° C. to about 200° C., preferably from about 20° C. to about 120° C. The products are isolated in a conventional manner. For example the catalyst is filtered off, the solvent evaporated and the product chromatographed.

Another method for the synthesis of compounds of formulas 1 and 11 involves heating compounds of formula 7 either alone or in an inert, organic solvent at from about 60° C. to about 350° C., preferably from about 80° C. to about 300° C. for from about ½ to about 72 hours, preferably from about 1 to about 24 hours. Typical inert, organic solvents that are used are those defined in the first method. The products are isolated by conventional techniques. For example, the reaction is diluted with a water-immiscible inert, organic solvent, washed with water dried and chromatographed.

Another method (hereinafter called the fifth method) of synthesis for compounds of formulas 1 and 11 involves reacting compounds of formula 8 with from about 0.8 to about 6, preferably from about 1 to about 3, molar equivalents of acyl derivatives of formula

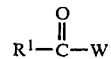

(where W is lower alkoxy, halogen, hydroxy or

in an optional inert organic solvent. Typical inert organic solvents which may be used include aryl hydrocarbons such as benzene, toluene, xylene and the like; chlorinated hydrocarbons such as tri- and tetrachloroethanes and the like; ethers such as 1,2-dimethoxyethane, tetrahydrofuran, dioxane and the like; N,N-dialkylformamides and alkyl alkanoylamides wherein the alkyl and alkanoyl radicals have 1-4 carbons such as dimethylformamide, dimethylacetamide and the like. Where W is lower alkoxy or hydroxy, suitable solvents also include lower alkanols of 1-6 carbons such as ethanol, t-butyl alcohol and n-butyl alcohol and the like and dimethyl sulfoxide. The reaction conditions and the isolation of the products are as described in the first method.

Another method for the synthesis of compounds of formulas 1 and 11 involves reacting compounds of formula 9 with at least about 0.1 preferably from at least about 0.8 to about 3 molar equivalents of an acyl derivative of formula

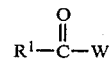

in the presence of at least about 0.1, preferably from at least about 0.8 to about 3, molar equivalents of an inorganic hydrohalic acid, preferably hydrogen bromide or hydrogen chloride. The reaction can optionally be run in an inert organic solvent. Where compounds of formula

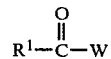

are "strong" carboxylic acids, such as chloroacetic, trifluoroacetic and oxalic acid and the like, the use of a hydrohalic acid is optional. Typical inert organic solvents include lower molecular weight ethers such as 1,2-dimethoxyethane, dioxane, tetrahydrofuran and the like; halogenated hydrocarbons such as methylene chloride, di-, tri- and tetrachloroethane and the like; nitroalkanes of 1-4 carbons such as nitromethane, nitroethane and the like; lower alkanols of 1-6 carbons such as ethanol, n-butanol and the like. The reaction is carried out at from about −50° C. to about 250° C., preferably from about +10° to about 180° C., for from about ¼ to about 96 hours, preferably from about ½ to about 48 hours. The products are isolated using conventional techniques as described in the first method.

Compounds of formula 1 where $R^2$ is lower acyloxy (of formula

or lower alkoxy (of formula —$OR^{13}$) can be prepared by reacting compounds of formula 1, where $R^2$ is halogen, with the appropriate acid of formula

(or alkali metal or tri-lower alkyl amine salt thereof) or with the appropriate alcohol of formula $HOR^{13}$ (or alkali metal salt thereof), respectively. The reaction is run in excess acid or alcohol, respectively, or, optionally, in an inert organic solvent such as ethers such as dioxane, tetrahydrofuran, 1,2-dimethoxyethane, and the like; N,N-dialkylformamides, N,N-dialkylalkanoyl amides wherein alkyl and alkanoyl radicals have 1-4 carbons, such as dimethyl formamide, dimethylacetamide and the like. The reaction is carried out for from about ¼ to about 72 hours, preferably about ½ to about 12 hours, at from about −20° C. to about 150° C., preferably about 20° C. to about 100° C. The The products are isolated by conventional techniques as described in the first method.

The compounds of formula 1 where $R^2$=OH are obtained by reacting compounds of formula 1 where $R^2$ is

with from about 0.2 to about 6, preferably about 0.8 to about 3, molar equivalents of an alkali metal (preferably sodium and potassium) hydroxide, bicarbonate or carbonate in an inert organic solvent, in optional presence of water. Suitable organic solvents include lower molecular weight alcohols, such as methanol, ethanol and the like; water-miscible ethers such as tetrahydrofuran, 1,2-dimethoxyethane, dioxane and the like; N,N-dialkylformamides, N,N-dialkyl alkanoylamides wherein the alkyl and alkanoyl radicals have 1-4 carbons such as dimethylformamide, dimethylacetamide, and the like. The reaction is carried out at from about −50° C. to about 100° C., preferably about −20° C. to about 70° C., for from about ¼ to about 72 hours, preferably about ½ to about 24 hours. The products are isolated in a conventional manner. For example, the reaction mixture is neutralized with acetic acid, evaporated and chromatographed.

The compounds of formula 1 where $R^2$ is halogen (preferably bromine or chlorine) are prepared by reacting compounds of formula 1 where $R^2$ is hydrogen with from about 0.5 to about 3, preferably from about 0.8 to about 1.3, molar equivalents of a lower alkyl N-haloamide, lower cycloalkyl N-haloimide or aryl sulfonyl N-haloamide, in the presence of a free radical catalyst, in an inert organic solvent. Suitable N-halo amides and imides include N-chloro and N-bromo-succinimide, and the like; N-chloroacetamide and the like; and N-chlorobenzenesulfonamide and the like. Suitable free radical catalysts include azobis-lower alkyl nitriles such as the preferred catalyst, azebisisobutyronitrile; di-lower alkyl peroxides such as di-t-butylperoxide; di-acyl peroxides such as acetyl peroxide; per esters such as t-butylperbenzoate; hydroperoxides such as t-butylhydroperoxide and the like. Typical inert organic solvents are aromatic hydrocarbons, such as benzene, toluene, xylene and the like; and chlorinated hydrocarbons such as methylene chloride, chlorobenzene, carbon tetrachloride, di-, tri- and tetrachloroethanes, chlorobenzene, and the like. The reaction is carried out at from about 25° C. to about 200° C., preferably at about the reflux temperature of the reaction medium, for from about ¼ to about 24 hours, preferably for from about ½ to about 5 hours. The product is isolated by conventional techniques. For example, the reaction mixture cooled to room temperature and evaporated.

Compounds of formula 1 where $R^2$ is alkyl of 1-4 carbons substituted by amino are prepared by reacting compounds of formula 1 where $R^2$ is hydrogen with from about 0.5 to about 12, preferably from about 0.8 to about 3.0 molar equivalents of an appropriate base, followed by reaction of the thus formed salt with a corresponding molar equivalent of an appropriate amino alkyl alkylating agent of formula $R^6$-M where $R^6$ is the amino alkyl moiety and M is halogen, preferably chlorine, bromine, iodine;

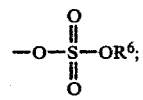

or an alkyl or arylsulfonate of formula

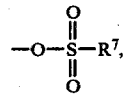

where $R^7$ can be alkyl of 1-6 carbons or aryl of from about 6 to 10 carbons optionally substituted by halogen, nitro or alkyl of 1-3 carbons, or $R^6$-M may be any other agent (within the definition of $R^6$) capable of introducing an aminoalkyl group. The reaction is run in an essentially inert organic solvent.

Typical bases include alkali metal (preferably sodium and potassium) salts as well as thallous salts of lower molecular weight alkanols of 1-6 carbons such as methanol, ethanol, propanol, isopropal, t-butanol, amyl alcohol and the like; alkali metal (preferably sodium) hydrides; alkali metals (preferably sodium and potassium); alkali metal (preferably sodium and potassium) salts of acidic hydrocarbons such as triphenylmethane and the like as well as any other base known to those skilled in the art for generating salts of acidic methylene groups. Typical organic solvents include those described in the first method.

The reaction is carried out at from about −20° C. to about 300° C., preferably from about 0° C. to about 100° C. for from about 0.2 hour to about 96 hours, preferably from about 0.5 hour to about 72 hours.

The products of formula 1 where $R^2$ is alkylamino are isolated by conventional techniques. For example the reaction mixture is evaporated; the residue is diluted with a water-immiscible, inert solvent such as methylene chloride, washed with water, dried and chromatographed.

Compounds of formula 1 can also be prepared by reacting compounds of formula 10 with at least from about 0.5 to a large excess, preferably at least from about 0.8 to about 100, molar equivalents of an aryl halide, in the presence of a copper catalyst, in an appropriate solvent containing from about 0.5 to about 1000, preferably about 0.8 to about 100, molar equivalents of an appropriate hydrogen halide acceptor. The preferred aryl halides are those of fromula AR-K where AR is phenyl optionally substituted by X and where K is preferably chlorine, bromine or iodine. The preferred copper catalysts are powdered copper metal, copper oxides and cuprous and cupric salts. Typical solvents include N,N-dialkylformamides and N,N-dialkyl alkanoyl amides wherein the alkyl and alkanoyl radicals have 1–4 carbons such as N,N-dimethylformamide, N,N-dimethylacetamide and the like; dialkyl sulfoxides of 2–6 carbons such as dimethyl sulfoxide and the like; and alkylphosphorous triamides of 4–10 carbons such as hexamethylphosphorous triamide. Appropriate hydrogen halide acceptors include alkali metal (preferably sodium or potassium) carbonates, bicarbonates, or lower alkyl carboxylic acid salts thereof (e.g., acetates). The reaction is carried out at from about 50° C. to about 200° C., preferably at from about 90° C. to about 180° C., for from about ¼ to about 72 hours, preferably for from about ½ to about 14 hours. The product is isolated in a conventional manner. For example, the reaction mixture is diluted with methylene chloride, washed with dilute aqueous ammonium hydroxide and chromatographed.

Compounds of formula 2 where m is one are prepared by reacting compounds of formula 17 where m is one with from about 0.5 to about 10, preferably about 0.8 to about 2, molar equivalents of a malonyl dihalide (preferably malonyl dichloride or malonyl dibromide) or an alkyl malonic acid derivative (of formula

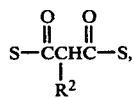

where S is halogen or —OR$^{13}$) in an inert organic solvent. Typical solvents are aromatic hydrocarbons such as benzene, toluene, xylene and the like; certain ethers such as dioxane, 1,2-dimethoxyethane, tetrahydrofuran and the like; chlorinated hydrocarbons such as di-, tri- and tetra-chloroethanes, chloroform, chlorobenzene, CCl$_4$, dichloroethane and the like; N,N-dialkylformamides and N,N-dialkyl alkanoylamides wherein the alkyl and alkanoyl radicals have 1–4 carbons such as N,N-dimethylformamide, N,N-dimethylacetamide and the like.

The reaction is carried out at from about −10° C. to about 200° C., preferably at from about +10° C. to about 140° C., for from about ¼ to about 92 hours, preferably for from about 1 to about 24 hours. The products are isolated in a conventional manner. For example, the solvent is partially evaporated and the product filtered off.

Compounds of formula 2 where m is one are also prepared by reacting compounds of formula 17 where m is one with from about 0.5 to about 3, preferably from about 0.8 to about 1.4, molar equivalents of a malonic acid of the formula

in an aqueous mineral acid. Typical mineral acids include sulfuric, hydrobromic and hydrochloric acid. The concentration of acid is from about 2 to about 7 normal, preferably from about 3.5 to about 4.5, normal. The reaction is carried out for from about ¼ to about 92 hours, preferably for from about ½ to about 24 hours at from about 40° C. to about 200° C., preferably from about 60° C. to about 140° C. The product is isolated in a conventional manner. For example, the reaction is cooled and the product filtered off.

Compounds of formula 2 where m is one are also prepared by reacting compounds of formula 13 where m is one in the optional presence of a catalyst in the optional presence of water in an organic solvent. Typical catalysts include inorganic acids such as hydrogen chloride, hydrogen bromide and sulfuric acid as well as bases such as alkali metal (preferably sodium and potassium) hydroxides and lower alkoxides and other conventional bases used for the condensation of an aryl amine with an alkyl carboxylic acid ester. Typical solvents include alkanols of 1–6 carbons such as methanol, ethanol and the like; certain water-miscible ethers such as tetrahydrofuran, dioxane and the like; N,N-dialkylformamides and N,N-dialkyl alkanoyl amides wherein the alkyl and alkanoyl radicals have 1–4 carbons such as N,N-dimethyl formamide, dimethylacetamide and the like. The reaction is carried out for from about ½ to about 96 hours, preferably for from about 1 to about 24 hours at from about −20° C. to about 150° C., preferably 0° C. to 100° C. The product is isolated in a conventional manner. For example the reaction is neutralized, diluted with a water-immiscible inert organic solvent, washed with water, dried and chromatographed.

Compounds of formula 2 where m is one are also prepared by reacting compounds of formula 14 where m is one with an appropriate reducing agent, in the presence of an acid or base catalyst, in the optional presence of water in an organic solvent. Typical reducing systems include powdered iron, zinc and tin in the presence of an aqueous acid, in an optional organic solvent. Typical acids include hydrohalic acids (preferably hydrochloric acid) and alkyl carboxylic acids of 1–6 carbon atoms such as acetic acid and the like. Typical solvent systems include aqueous alkanols of 1–6 carbons such as methanol, ethanol and the like. Still other reducing agents include stannous chloride and aqueous hydrochloric acid; sodium hydrosulfite; ferrous sulfate and ammonium hydroxide; ammonium sulfide; hydrazine in the presence of palladized charcoal; sodium sulfide and ammonium chloride, sodium sulfide and sulfur. The reaction is carried out at from about 0° C. to about 200° C., preferably at from about 10° C. to about 140° C. for from about 1/6 to about 92 hours, preferably for from about ½ to about 24 hours. The products are isolated by conventional techniques. For example the reaction is filtered, evaporated, saponified in alcoholic potassium hydroxide, evaporated, taken up in water, adjusted to pH 6 and the product filtered off and chromatographed.

Compounds of formula 2, where m is zero are prepared from compounds of formulas 13, 14 and 17 where m is zero by the methods described for the preparation of compounds of formula 2, where m is one [see also: Chemical Reviews, 68, 780ff(1968) and references cited therein and, S. African Pat. No. 6,800,803 (1968)].

Compounds of formula 3 can be prepared by reacting compounds of formula 2 with from about 0.5 to about 2.0, preferably with from about 0.9 to about 1.2, molar equivalents of phosphorous pentasulfide in an aprotic, essentially inert organic solvent. Typical inert organic solvents include aryl hydrocarbons such as benzene, toluene or xylene; aliphatic hydrocarbons of 5–12 carbons, such as hexane, heptane and the like; alicyclic hydrocarbons of 5–8 carbons, such as cyclohexane and the like; basic carbocyclic amines such as pyridine, quinoline, γ-picoline and the like; and any other conventional solvent materials which are relatively inert with regard to the starting materials.

The reaction is carried out at from about 10° C. to about 250° C., preferably at from about 50° C. to about 150° C., for from about 5 minutes to about 72 hours, preferably from about 10 minutes to about 6 hours. The product of formula 3 is isolated by conventional techniques. For example the reaction solvent is evaporated, the residue stirred with ice water, extracted into a water-immiscible organic solvent; the water-immiscible solvent is washed consecutively with water, dilute aqueous hydrohalic acid, dried and chromatographed.

Compounds of formula 4 are prepared by reacting compounds of formula 3 with from about 0.5 to about 6, preferably from about 0.8 to about 1.2, molar equivalents of an alkylating agent of formula $R^3$-M [where M may be halogen, preferably bromine or iodine;

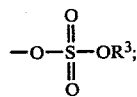

or an alkyl or arylsulfonate moiety of formula

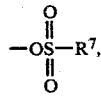

where $R^7$ can be alkyl of 1–6 carbons or aryl of from 6 to 10 carbons optionally substituted by halogen, nitro or alkyl of 1–3 carbons or $R^3$-M may be any other agent (within the definition of $R^3$) capable of selectively alkylating the sulfur atom in the presence of the other groups in 3] in the presence of an appropriate base in an inert organic solvent. Typical bases include alkali metal hydroxides (preferably sodium and potassium hydroxide), alkali metal carbonates (preferably sodium and potassium bicarbonate or carbonate) and appropriate organic tertiary amines such as trialkylamines, e.g., triethylamine and the like, and pyridine and the like. Typical solvents include lower molecular weight alkanols of 1–6 carbons such as methanol, ethanol and the like; water-miscible ethers such as dioxane, tetrahydrofuran, 1,2-dimethoxyethane and the like; N,N-dialkylformamides and N,N-dialkyl alkanoyl amides wherein the alkyl and alkanoyl radicals have 1–4 carbons such as dimethyl formamide or dimethylacetamide and the like; alkyl ketones of 2–5 carbons such as acetone, methylethylketone and the like, and dimethyl sulfoxide. The reaction is carried out at from about −60° C. to about 150° C., preferably at from about 0° C. to about 90° C., for from about 1 minute to about 90 hours, preferably for from about 5 minutes to about 24 hours. The products of formula 4 are isolated by conventional techniques. For example, the reaction is diluted with water, extracted with a water-immiscible solvent, dried and chromatographed.

Compounds of formula 5 can be prepared by reacting compounds of formula 2 with from about 0.5 to about 3, preferably with from about 0.8 to about 1.2, molar equivalents of a suitable halogenating agent in an inert organic solvent, in the optional presence of an acid proton acceptor. Typical halogenating agents include the phosphorous halides such as phosphorous pentachloride, phosphorous oxychloride, and phosphorous oxybromide. Typical inert organic solvents include aromatic hydrocarbons such as benzene, toluene, xylene and the like; chlorinated hydrocarbons such as methylene chloride, chloroform, chlorobenzene, CCl₄, di-, tri- and tetrachloroethanes and the like. Phosphorous oxyhalides such as phosphorous oxychloride and the like can be used both as solvent and halogenating agent.

Optional acid proton acceptors include N,N-di-lower alkyl aryl amines such as N,N-dimethylaniline, N,N-diethylaniline and the like and trialkylamines such as triethylamine, tributylamine and the like.

The reaction is carried out at from about 0° C. to about 200° C., preferably at from about 40° C. to about 150° C., for from about ¼ to about 72 hours, preferably for from ½ to about 24 hours. The products of formula 5 are isolated by conventional techniques. For example, the reaction mixture is evaporated and the residue is diluted with an aprotic, inert, organic solvent, washed with cold water, and then evaporated. The residual product is stirred with a non-solubilizing inert organic solvent, such as carbon tetrachloride, and the product is filtered off.

Compounds of formula 6 are prepared by reacting compounds of formula 2 with from about 0.8 to about 50, preferably from 1 to about 20, molar equivalents of a diazo-lower alkane in an inert organic solvent. Typical inert organic solvents include lower molecular weight ethers such as diethyl ether, tetrahydrofuran, dioxane, 1,2-dimethoxyethane and the like; alkanols of 1–6 carbons such as methanol, ethanol and the like and halogenated hydrocarbons such as chloroform methylene chloride, CCl₄, 1,2-dichloroethane, chlorobenzene, di-, tri- and tetrachloroethanes and the like.

The reaction is carried out at from about −50° C. to about 100° C., preferably at from about 0° C. to about 60° C., for from about ¼ hour to about 72 hours, preferably for from about ½ to about 12 hours.

The products of formula 6 are isolated by conventional techniques. For example, the reaction is filtered, evaporated and chromatographed.

Another method for the preparation of compounds of formula 6 involves reacting compounds of formula 2 with from about 0.5 to about 3, preferably with from about 0.8 to about 1.4, molar equivalents of a tri-lower alkyl oxonium fluoroborate in an inert organic solvent. Typical solvents include halogenated hydrocarbons such as methylene chloride, CCl₄, chloroform, 1,2-dichloroethane, chlorobenzene, di-, tri- and tetrachloroethanes and the like. The reaction is carried out at from about −50° C. to about 100° C., preferably at from about −20° C. to about 70° C. for from about ½ hour to about 72 hours preferably for from about 1 to about 24 hours.

The products of formula 6 are isolated by conventional techniques. For example, the reaction mixture is washed with cold aqueous potassium bicarbonate, dried and the solvent evaporated.

Compounds of formula 7 are prepared by reacting compounds of formulas 3-6 with from about 0.8 to about 6.0, preferably with from about 1 to about 3, molar equivalents of an acid hydrazide of formula

in an inert organic solvent. Typical solvents include alkanols of 1-6 carbons such as methanol, ethanol, t-butanol, n-butanol and the like; aromatic hydrocarbons such as benzene, toluene, xylene and the like; chlorinated hydrocarbons such as methylene chloride, chloroform, di-, tri- and tetrachloroethane and the like; ethers such as tetrahydrofuran, dioxane, 1,2-dimethoxyethane and the like; N,N-dialkylformamides, N,N-dialkyl alkanoyl amides wherein the alkyl and alkanoyl radicals have from 1-4 carbons, such as N,N-dimethyl formamide, N,N-dimethylacetamide and the like; hexamethylenephosphorous triamide and dimethyl sulfoxide. The reaction is carried out at from about $-30°$ C. to about $160°$ C. preferably at from about $30°$ C. to about $120°$ C., for from about $\frac{1}{2}$ to about 96 hours, preferably for from about 2 to about 12 hours. The products of formula 7 are isolated by conventional techniques. For example, the reaction is diluted with a water-immiscible inert organic solvent, washed with water, dried and chromatographed.

Compounds of formula 8 are prepared by reacting compounds of formula 9 with at least about 0.1 preferably from about 0.8 to about 3, molar equivalents of an inorganic hydrohalic acid, referably hydrogen bromide or hydrogen chloride in an inert organic solvent. Typical inert organic solvents include alkanols of 1-6 carbons such as ethanol, t-butanol and the like; lower molecular weight ethers such as dioxane, tetrahydrofuran, diethyl ether, 1,2-dimethoxyethane and the like; chlorinated hydrocarbons such as methylene chloride, $CCl_4$, chlorobenzene, di-, tri-, and tetrachloroethanes, chloroform and the like; N,N-dialkylformamides, N,N-dialkyl alkanoyl amides wherein the alkyl and alkanoyl radicals have 1-4 carbons, such as dimethyl formamide, dimethylacetamide and the like. The reaction is run for from about $\frac{1}{4}$ to about 90 hours, preferably for from about $\frac{1}{2}$ to about 3 hours, at from about $-50°$ C. to about $100°$ C., preferably at from about $-30°$ C. to about $80°$ C. The products are isolated by conventional techniques. For example, the solvent is evaporated at room temperature in vacuo, the residue stirred in cold water containing an alkali metal hydroxide, equivalent in molar amount to the amount of hydrohalic acid used, and the product is then removed by filtration and dried.

Compounds of formula 9 are prepared by reacting compounds of formulas 3-6 with from about 0.5 to about 6, preferably with from about 0.8 to about 3, molar equivalents of a compound of formula

in an inert organic solvent. Typical solvents are those as defined in the first method. The reaction is carried out at from about $40°$ C. to about $250°$ C., preferably at from about $50°$ C. to about $180°$ C. for from about $\frac{1}{4}$ hours to about 92 hours, preferably about 1 to about 48 hours. The products of formula 9 are isolated by conventional techniques as described in the first method.

Compounds of formula 10 are prepared by the removal of the $N^6$ benzyl group in compounds of formula 11 wherein the benzyl group is replaced by hydrogen. Suitable reagents and conditions are those described below for the debenzylation of compounds of formula 12. The isolation of the products is as exemplified for compounds of formula 12.

Compounds of formula 12 are prepared by reacting compounds of formulas 3-6 wherein m is zero with from about 0.5 to about 6, preferably with from about 0.8 to about 3, molar equivalents of an acid hydrazide of formula

in an inert organic solvent. Typical solvents, the conditions of the reaction and the isolation of the product are as described in the first method.

Compounds of formula 13 are prepared by reacting compounds of formula 14 with an appropriate reducing agent under selective conditions in an inert organic solvent.

Typical reducing agents include a metal catalyst, preferably Raney nickel, and hydrogen in the optional presence of a hydrogen halide in an inert organic solvent. Typical solvents include alkanols of 1-6 carbons such as methanol, ethanol and the like. The preferred optional hydrogen halides are hydrogen chloride and hydrogen bromide. The reactions are carried out for from about 1/6 hour to about 92 hours, preferably for from about $\frac{1}{2}$ to about 24 hours at from about $0°$ C. to about $150°$ C., preferably at from about $10°$ C. to about $120°$ C. Hydrogen pressures are from about 0.1 to about 100 atm. preferably about 0.8 to about 10 atm. The reaction is stopped after approximately three molar equivalents of hydrogen have been absorbed. The products are isolated in a conventional manner. For example the reaction is filtered, made alkaline to pH 8, extracted with a water-miscible organic solvent, washed with water, dried and chromatographed.

Compounds of formula 14 are prepared by reacting compounds of formula 15 with from about 0.5 to about 6, preferably with from about 0.8 to about 2, molar equivalents of a compound of formula 16 (where B is halogen, preferably chlorine or bromine, or a group of formula

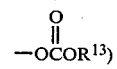

in an inert organic solvent. Typical solvents include aromatic hydrocarbons such as benzene, toluene, xylene and the like; halogenated hydrocarbons such as chloroform, methylene chloride, $CCl_4$, chlorobenzene, di-, tri- and tetrachloroethane and the like; certain ethers such as 1,2-dimethoxyethane, dioxane, tetrahydrofuran and the like; N,N-dialkylformamides, N,N-dialkyl alkanoyl amides wherein the alkyl and alkanoyl radicals have 1-4 carbons, such as N,N-dimethyl amide and the like. The reactions are carried out for from about ½ to about 92 hours, preferably for from about 2 to about 24 hours at from about −20° C. to about 150° C., preferably at from about +5° C. to about 100° C. The products are isolated by conventional techniques as examplified in the first method.

Compounds of formula 17 are prepared by reacting compounds of formula 15 with an appropriate reducing agent in an essentially inert organic solvent. Typical reducing agents include a metal catalyst such as palladium, platinum and the preferred catalyst Raney nickel in the presence of hydrogen in the optional presence of a hydrogen halide (preferably hydrogen chloride and hydrogen bromide). Typical solvents include alkanols of 1 to 6 carbons such as methanol, ethanol, propanol, isopropanol and the like.

Hydrogen pressures are from about 0.1 to about 100 atm., preferably from about 0.8 to about 10 atm. The reaction is stopped after approximately three molar equivalents of hydrogen have been absorbed.

The reaction is carried out at from about 0° C. to about 150° C., preferably from about 20° C. to about 100° C. for from about 0.2 hour to about 96 hours, preferably from about 0.5 hour to about 24 hours.

The products of formula 17 are isolated by conventional techniques. For example the reaction is filtered, made alkaline to pH 8, diluted with a water-immiscible, inert organic solvent, washed with water, dried and evaporated.

Compounds of formula 15 are prepared by reacting compounds of formula 18 with at least about 0.2 molar equivalents, preferably from about 0.8 to about 100 molar equivalents of a compound of formula 19 in the optional presence of a hydrogen halide acceptor in the optional presence of an inert organic solvent.

Typical hydrogen halide acceptors include alkali metal (preferably sodium or potassium) carbonates, bicarbonates, or lower alkyl carboxylic acid salts thereof (e.g., acetates).

Typical solvents include nitrohydrocarbons such as nitrobenzene and the like; lower alkanols of 1–6 carbons such as ethanol, t-butanol, butanol and the like.

The reaction is carried out at from about 25° C. to about 300° C., preferably from about 50° C. to about 250° C. for from about 0.2 hour to about 96 hours, preferably from about 1 hour to about 48 hours.

The products of formula 15 are isolated by conventional techniques. For example the reaction is poured into excess dilute hydrochloric acid and extracted with ether. For products of formula 15 where m is zero, the ether is dried, evaporated and the residual crude product is chromatographed.

For products of formula 15 where m is one, the above obtained aqueous hydrochloric acid extract is made alkaline to pH 9 and extracted with ether. The ether is dried, evaporated and the residual product is chromatographed.

For compounds of formula 15 where m is zero see also Chemical Abstracts, 43, 6175d (1948).

For compounds of formula 15 where m is one see also Proc. Indian Acad. Sci., 47A, 77 (1958).

For compounds of formula 16 see Acta Chem. Scand., 15,260 (1961).

The novel compounds of formula I are CNS depressants and are useful as, for example, sedatives, tranquilizers, hypnotics, anticonvulsants and muscle relaxants in mammalian species, e.g. rats, mice and monkeys. They are also useful as feed additives for increasing growth rate and feed efficiency in mammalian species, such as livestock, specifically swine and cattle. The CNS depressant effects of compounds of this invention are shown, for example, by the following tests in animals. Thus, for example, oral administration of a compound of the invention produces ataxia at dosage levels of from about 0.1 to about 10 mg/kg, specifically, in rats at about 3.1 mg/kg, in mice at about 1 mg/kg and in monkeys at about 2.5 mg/kg.

The compounds of the present invention produce a significant tranquilizing effect at a dosage level of from about 0.1 to about 25 mg/kg, specifically at a dosage level of about 6.2 mg/kg when administered via the oral route to rats in a conflict test procedure [cf. J. R. Vogel, B. Beer, D. Clody, Psychopharmacologist, 21, 1 (1970)].

In mice, oral administration of from about 0.1 to about 50 mg/kg of a compound of the present invention antagonizes the convulsant effects of subcutaneously administered pentylenetetrazole and of intraveneously administered strychnine.

Mice treated with from about 0.01 to about 200 mg/kg of a compound of the present invention via the oral route increase significantly their food consumption.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 10 and 500 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agents such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially nontoxic in the amounts employed.

In the following examples all reactions are run under an inert atmosphere (e.g. argon), at room temperature, using anhydrous solvents unless otherwise indicated; in addition, reactions which are heated are subsequently cooled to room temperature for work-up. In general, solvents are evaporated in a rotary flash vacuum apparatus. In this patent application, the full name of the parent ring system of compounds described as indicated in Column I below is as indicated in Column II.

| I | II |
| --- | --- |
| "---4H-s-triazolo[4,3-a][1,5]-benzodiazepin---" | "---5,6-dihydro-4H-s-triazolo[4,3-a][1,5]-benzodiazepin---" |
| "---1H-1,5-benzodiazepin---" | "---2,3,4,5-tetrahydro-1H-1,5-benzodiazepin---" |
| "---3H-1,5-benzodiazepin---" | "---4,5-dihydro-3H-1,5-benzodiazepin---" |

EXAMPLE 1

7-chloro-5-phenyl-1H-1,5-benzodiazepin-4-one-2-thione

A solution of 28.6 g of 7-chloro-5-phenyl-1H-1,5-benzodiazepine-2,4-dione and 23.3 g of phosphorous pentasulfide in 250 ml of pyridine is refluxed, with stirring, for 40 minutes under argon. The solvent is evaporated in vacuo.

The residue is stirred in ice water and extracted with methylene chloride. The organic phase is washed consecutively with dilute aqueous hydrochloric acid, water and dried. The organic phase is filtered through a short column of neutral III alumina, the column is washed with ethyl acetate and the filtrate evaporated. The residue is triturated with a small amount of hot benzene and the product filtered off and dried.

EXAMPLES 2–28

Following the procedure of Example 1 but substituting the compounds indicated in Column I below for 7-chloro-5-phenyl-1H-1,5-benzodiazepine-2,4-dione in Example 1, the compounds indicated in Column II are obtained:

| | I | II |
| --- | --- | --- |
| 2. | 5-phenyl-1H-1,5-benzodiazepine-2,4-dione | 5-phenyl-1H-1,5-benzodiazepin-4-one-2-thione |
| 3. | 7-(trifluoromethyl)-5-phenyl-1H-1,5-benzodiazepine-2,4-dione | 7-(trifluoromethyl)-5-phenyl-1H-1,5-benzodiazepin-4-one-2-thione |
| 4. | 7-nitro-5-phenyl-1H-1,5-benzodiazepine-2,4-dione | 7-nitro-5-phenyl-1H-1,5-benzodiazepin-4-one-2-thione |
| 5. | 7-methyl-5-phenyl-1H-1,5-benzodiazepine-2,4-dione | 7-methyl-5-phenyl-1H-1,5-benzodiazepin-4-one-2-thione |
| 6. | 7-methoxy-5-phenyl-1H-1,5-benzodiazepine-2,4-dione | 7-methoxy-5-phenyl-1H-1,5-benzodiazepin-4-one-2-thione |
| 7. | 7-(methylthio)-5-phenyl-1H-1,5-benzodiazepine-2,4-dione | 7-(methylthio)-5-phenyl-1H-1,5-benzodiazepin-4-one-2-thione |
| 8. | 7-pentyl-5-phenyl-1H-1,5-benzodiazepine-2,4-dione | 7-pentyl-5-phenyl-1H-1,5-benzodiazepin-4-one-2-thione |
| 9. | 7-pentoxy-5-phenyl-1H-1,5-benzodiazepine-2,4-dione | 7-pentoxy-5-phenyl-1H-1,5-benzodiazepin-4-one-2-thione |
| 10. | 7-bromo-5-phenyl-1H-1,5-benzodiazepine-2,4-dione | 7-bromo-5-phenyl-1H-1,5-benzodiazepin-4-one-2-thione |
| 11. | 7-fluoro-5-phenyl-1H-1,5-benzodiazepine-2,4-dione | 7-fluoro-5-phenyl-1H-1,5-benzodiazepin-4-one-2-thione |
| 12. | 7-cyano-5-phenyl-1H-1,5-benzodiazepine-2,4-dione | 7-cyano-5-phenyl-1H-1,5-benzodiazepin-4-one-2-thione |
| 13. | 7-chloro-5-(2-chlorophenyl)-1H-1,5-benzodiazepine-2,4-dione | 7-chloro-5-(2-chlorophenyl)-1H-1,5-benzodiazepin-4-one-2-thione |
| 14. | 7-chloro-5-(2-fluorophenyl)-1H-1,5-benzodiazepine-2,4-dione | 7-chloro-5-(2-fluorophenyl)-1H-1,5-benzodiazepin-4-one-2-thione |
| 15. | 7-chloro-5-(3-chlorophenyl)-1H-1,5-benzodiazepine-2,4-dione | 7-chloro-5-(3-chlorophenyl)-1H-1,5-benzodiazepin-4-one-2-thione |
| 16. | 7-chloro-5-(4-chlorophenyl)-1H-1,5-benzodiazepine-2,4-dione | 7-chloro-5-(4-chlorophenyl)-1H-1,5-benzodiazepin-4-one-2-thione |
| 17. | 7-chloro-5-(2-methoxyphenyl)-1H-1,5-benzodiazepine-2,4-dione | 7-chloro-5-(2-methoxyphenyl)-1H-1,5-benzodiazepin-4-one-2-thione |
| 18. | 7-chloro-5-(3-methoxyphenyl)-1H-1,5-benzodiazepine-2,4-dione | 7-chloro-5-(3-methoxyphenyl)-1H-1,5-benzodiazepin-4-one-2-thione |
| 19. | 7-chloro-5-(4-methoxyphenyl)-1H-1,5-benzodiazepine-2,4-dione | 7-chloro-5-(4-methoxyphenyl)-1H-1,5-benzodiazepin-4-one-2-thione |
| 20. | 7-chloro-5-(2-methylphenyl)-1H-1,5-benzodiazepine-2,4-dione | 7-chloro-5-(2-methylphenyl)-1H-1,5-benzodiazepin-4-one-2-thione |
| 21. | 7-chloro-5-(3-methylphenyl)-1H-1,5-benzodiazepine-2,4-dione | 7-chloro-5-(3-methylphenyl)-1H-1,5-benzodiazepin-4-one-2-thione |
| 22. | 7-chloro-5-(4-methylphenyl)-1H-1,5-benzodiazepine-2,4-dione | 7-chloro-5-(4-methylphenyl)-1H-1,5-benzodiazepin-4-one-2-thione |
| 23. | 3-methyl-7-chloro-5-phenyl-1H-1,5-benzodiazepine-2,4-dione | 3-methyl-7-chloro-5-phenyl-1H-1,5-benzodiazepin-4-one-2-thione |
| 24. | 3-(benzyloxy)-7-chloro-5-phenyl-1H-1,5-benzodiazepine-2,4-dione | 3-(benzyloxy)-7-chloro-5-phenyl-1H-1,5-benzodiazepin-4-one-2-thione |
| 25. | 3-methoxy-7-chloro-5-phenyl-1H-1,5-benzodiazepine-2,4-dione | 3-methoxy-7-chloro-5-phenyl-1H-1,5-benzodiazepin-4-one-2-thione |
| 26. | 8-methyl-5-phenyl-1H-1,5-benzodiazepine-2,4-dione | 8-methyl-5-phenyl-1H-1,5-benzodiazepin-4-one-2-thione |
| 27. | 8-chloro-5-phenyl-1H-1,5-benzodiazepine-2,4-dione | 8-chloro-5-phenyl-1H-1,5-benzodiazepin-4-one-2-thione |
| 28. | 8-(trifluoromethyl)-5-phenyl-1H-1,5-benzodiazepine-2,4-dione | 8-(trifluoromethyl)-5-phenyl-1H-1,5-benzodiazepin-4-one-2-thione |

EXAMPLE 29

1-Methyl-8-chloro-6-phenyl-4H-s-triazolo[4,3-a][1,5]-benzodiazepin-5-one

Method A 30.2 g of 7-chloro-5-phenyl-1H-1,5-benzodiazepin-4-one-2-thione and 23.8 g of acetic acid hydrazide in a mixture of 640 ml n-butanol and 160 ml of dimethyl sulfoxide are refluxed with stirring for 24 hours. During this time, argon is bubbled through the reaction mixture. The reaction is concentrated in vacuo and partitioned between methylene chloride and water; the organic phase is washed several times with water, dried and filtered through a short Florisil column. After eluting the column with ethyl acetate, the combined filtrates are evaporated to give the title compound. Recrystallization from ethanol-ethyl acetate, followed by vacuum drying at elevated temperatures gives the product.

Method B 15.8 g of 2-(methylthio)-7-chloro-5-phenyl-3H-1,5-benzodiazepin-4-one and 8.1 g of acetic acid hydrazide in 400 ml dimethyl formamide are refluxed with stirring for 24 hours. During this time nitrogen is bubbled through the reaction mixture. The reaction mixture is worked up as described in Example 29, method A, to give the title compound.

Method C

A mixture of 6.2 g of 1-methyl-8-chloro-4H-s-triazolo[4,3-a][1,5]benzodiazepin-5-one, 5 g of copper powder and 2.5 g of potassium acetate in 100 ml bromobenzene are refluxed for six hours with stirring. The reaction is diluted with methylene chloride, filtered through a short Florisil column and the filtrate washed with dilute aqueous ammonium hydroxide. The organic phase is washed with water, dried and the solvent evaporated to give the title compound.

Method D 3.0 g of 2,7-dichloro-5-phenyl-3H-1,5-benzodiazepin-4-one and 1.8 g of acetic acid hydrazide in 50 ml of dioxane are refluxed under argon for 24 hours. 2 ml of water is then added, the reaction stirred for 1 hour and the solvent evaporated. The residue is taken up in methylene chloride, washed with dilute aqueous sodium bicarbonate, with water and dried. The solvent is evaporated and the residue is chromatographed on ten-1000μ silica gel thick layer plates (20×20 cm) with ethyl acetate-ethanol (9:1) as eluant. The main band, having an approximate Rf range of 0.12-0.28, is removed, stirred with acetone-methanol (9:1) and the silica gel filtered off. The filtrate is evaporated to give the title compound.

Method E

Following the procedure of Example 29, Method B, but substituting 15 g of 2-methoxy-7-chloro-5-phenyl-3H-1,5-benzodiazepin-4-one for 15.8 g of 2-(methylthio)-7-chloro-5-phenyl-3H-1,5-benzodiazepin-4-one in Example 29, Method B, the title compound is obtained.

Method F 15 g of acetic acid 2-(7-chloro-5-phenyl-3H-1,5-benzodiazepin-4-one-2-yl)hydrazide in 100 ml dimethyl formamide are refluxed for 24 hours under a Soxhlet extractor containing 4A molecular sieves, under argon. The solvent is evaporated and the crude product is purified as described in Example 29, Method D.

Method G 3.01 g of 2-hydrazino-7-chloro-5-phenyl-3H-1,5-benzodiazepin-4-one in 15 ml of acetic anhydride is refluxed for 24 hours. The acetic anhydride is evaporated and the residual crude product taken up in methylene chloride and purified as described in Example 29, Method D.

Method H 4.0 g of 2-[2-(t-butoxycarbonyl)hydrazino]-7-chloro-5-phenyl-3H-1,5-benzodiazepin-4-one in 60 ml of n-butyl acetate which contains 2.0 g of hydrogen bromide is stirred at room temperature for 1 hour and refluxed for 24 hours. The reaction is evaporated, the product dissolved in methylene chloride and purified as described in Example 29, Method D.

Method I

To 4.96 g of 1-methyl-8-chloro-4H-s-triazolo[4,3-a][1,5]benzodiazepin-5-one in a mixture of 70 ml ethanol and 200 ml of 0.1 N aqueous potassium hydroxide is added 7.2 g of diphenyliodonium bromide. The reaction is refluxed for 8 hours. The iodobenzene is removed by steam distillation. The distillation residue is cooled and partitioned between methylene chloride and water. The organic phase is dried and evaporated to give the title compound.

EXAMPLES 30–55

Following the procedure of Example 29, Method A, but substituting the compounds indicated in Column I below for 7-chloro-5-phenyl-1H-1,5-benzodiazepin-4-one-2-thione in Example 29, Method A, the compounds indicated in Column II are obtained.

| | I | II |
|---|---|---|
| 30. | 5-phenyl-1H-1,5-benzodiazepin-4-one-2-thione | 1-methyl-6-phenyl-4H-s-triazolo[4,3-a][1,5]benzodiazepin-5-one |
| 31. | 7-(trifluoro-methyl)-5-phenyl-1H-1,5-benzodiazepin-4-one-2-thione | 1-methyl-8-(trifluoromethyl)-6-phenyl-4H-s-triazolo[4,3-a][1,5]benzodiazepin-5-one |
| 32. | 7-nitro-5-phenyl-1H-1,5-benzodiazepin-4-one-2-thione | 1-methyl-8-nitro-6-phenyl-4H-s-triazolo[4,3-a][1,5]benzodiazepin-5-one |
| 33. | 7-methyl-5-phenyl-1H-1,5-benzodiazepin-4-one-2-thione | 1-methyl-8-methyl-6-phenyl-4H-s-triazolo[4,3-a][1,5]benzodiazepin-5-one |
| 34. | 7-methoxy-5-phenyl-1H-1,5-benzodiazepin-4-one-2-thione | 1-methyl-8-methoxy-6-phenyl-4H-s-triazolo[4,3-a][1,5]benzodiazepin-5-one |
| 35. | 7-(methylthio)-5-phenyl-1H-1,5-benzodiazepin-4-one-2-thione | 1-methyl-8-(methylthio)-6-phenyl-4H-s-triazolo[4,3-a][1,5]benzodiazepin-5-one |
| 36. | 7-pentyl-5-phenyl-1H-1,5-benzodiazepin-4-one-2-thione | 1-methyl-8-pentyl-6-phenyl-4H-s-triazolo[4,3-a][1,5]benzodiazepin-5-one |
| 37. | 7-pentoxy-5-phenyl-1H-1,5-benzodiazepin-4-one-2-thione | 1-methyl-8-pentoxy-6-phenyl-4H-s-triazolo[4,3-a][1,5]benzodiazepin-5-one |
| 38. | 7-bromo-5-phenyl-1H-1,5-benzodiazepin-4-one-2-thione | 1-methyl-8-bromo-6-phenyl-4H-s-triazolo[4,3-a][1,5]benzodiazepin-5-one |
| 39. | 7-fluoro-5-phenyl-1H-1,5-benzodiazepin-4-one-2-thione | 1-methyl-8-fluoro-6-phenyl-4H-s-triazolo[4,3-a][1,5]benzodiazepin-5-one |
| 40. | 7-cyano-5-phenyl-1H-1,5-benzodiazepin-4-one-2-thione | 1-methyl-8-cyano-6-phenyl-4H-s-triazolo[4,3-a][1,5]benzodiazepin-5-one |
| 41. | 7-chloro-5-(2-chlorophenyl)-1H-1,5-benzodiazepin-4-one-2-thione | 1-methyl-8-chloro-6-(2-chlorophenyl)-4H-s-triazolo[4,3-a][1,5]benzodiazepin-5-one |
| 42. | 7-chloro-5-(2-fluorophenyl)-1H-1,5-benzodiazepin-4-one-2-thione | 1-methyl-8-chloro-6-(2-fluorophenyl)-4H-s-triazolo[4,3-a][1,5]benzodiazepin-5-one |
| 43. | 7-chloro-5-(3-chlorophenyl)-1H-1,5-benzodiazepin-4-one-2-thione | 1-methyl-8-chloro-6-(3-chlorophenyl)-4H-s-triazolo[4,3-a][1,5]benzodiazepin-5-one |
| 44. | 7-chloro-5-(4-chlorophenyl)-1H-1,5-benzodiazepin-4-one-2-thione | 1-methyl-8-chloro-6-(4-chlorophenyl)-4H-s-triazolo[4,3-a][1,5]benzodiazepin-5-one |
| 45. | 7-chloro-5-(2-methoxyphenyl)-1H-1,5-benzodiazepin-4-one-2-thione | 1-methyl-8-chloro-6-(2-methoxyphenyl)-4H-s-triazolo[4,3-a][1,5]benzodiazepin-5-one |
| 46. | 7-chloro-5-(3-methoxyphenyl)-1H-1,5-benzodiazepin-4-one-2-thione | 1-methyl-8-chloro-6-(3-methoxyphenyl)-4H-s-triazolo[4,3-a][1,5]- |

| | I | II |
|---|---|---|
| 47. | 7-chloro-5-(2-methyl-phenyl)-1H-1,5-benzo-diazepin-4-one-2-thione | 1-methyl-8-chloro-6-(2-methylphenyl)-4H-s-triazolo[4,3-a][1,5]-benzodiazepin-5-one |
| 48. | 7-chloro-5-(3-methyl-phenyl)-1H-1,5-benzo-diazepin-4-one-2-thione | 1-methyl-8-chloro-6-(3-methylphenyl)-4H-s-triazolo[4,3-a][1,5]-benzodiazepin-5-one |
| 49. | 7-chloro-5-(4-methyl-phenyl)-1H-1,5-benzo-diazepin-4-one-2-thione | 1-methyl-8-chloro-6-(4-methylphenyl)-4H-s-triazolo[4,3-a][1,5]-benzodiazepin-5-one |
| 50. | 3-methyl-7-chloro-5-phenyl-1H-1,5-benzo-diazepin-4-one-2-thione | 1,4-dimethyl-8-chloro-6-phenyl-4H-s-triazolo[4,3-a][1,5]-benzodiazepin-5-one |
| 51. | 3-(benzyloxy)-7-chloro-5-phenyl-1H-1,5-benzodia-zepin-4-one-2-thione | 4-(benzyloxy)-1-methyl-8-chloro-6-phenyl-4H-s-triazolo[4,3-a][1,5]-benzodiazepin-5-one |
| 52. | 3-methoxy-7-chloro-5-phenyl-1H-1,5-benzo-diazepin-4-one-2-thione | 4-(methoxy)-1-methyl-8-chloro-6-phenyl-4H-s-triazolo[4,3-a][1,5]-benzodiazepin-5-one |
| 53. | 8-methyl-5-phenyl-1H-1,5-benzodiazepin-4-one-2-thione | 1,9-dimethyl-6-phenyl-4H-s-triazolo[4,3-a]-[1,5]benzodiazepin-5-one |
| 54. | 8-chloro-5-phenyl-1H-1,5-benzodiazepin-4-one-2-thione | 9-chloro-1-methyl-6-phenyl-4H-s-triazolo-[4,3-a][1,5]-benzodiazepin-5-one |
| 55. | 8-(trifluoromethyl)-5-phenyl-1H-1,5-benzo-diazepin-4-one-2-thione | 9-(trifluoromethyl)-1-methyl-6-phenyl-4H-s-triazolo[4,3-a][1,5]-benzodiazepin-5-one |

EXAMPLES 56–64

Following the procedure of Example 29, Method A, but substituting the acid hydrazides indicated in Column I below for acetic acid hydrazide in Example 29, Method A, the compounds indicated in Column II are obtained.

| | I | II |
|---|---|---|
| 56. | formic acid hydrazide | 8-chloro-6-phenyl-4H-s-triazolo[4,3-a][1,5]-benzodiazepin-5-one |
| 57. | propionic acid hydrazide | 1-ethyl-8-chloro-6-phenyl-4H-s-triazolo-[4,3-a][1,5]benzodiaze-pin-5-one |
| 58. | valeric acid hydrazide | 1-butyl-8-chloro-6-phenyl-4H-s-triazolo-[4,3-a][1,5]benzodia-zepin-5-one |
| 59. | cyclopropane carboxylic acid hydrazide | 1-cyclopropyl-8-chloro-6-phenyl-4H-s-triazolo-[4,3-a][1,5]benzodia-zepin-5-one |
| 60. | cyclopentane carboxylic acid hydrazide | 1-cyclopentyl-8-chloro-6-phenyl-4H-s-triazolo-[4,3-a][1,5]benzodia-zepin-5-one |
| 61. | phenylacetic acid hydrazide | 1-benzyl-8-chloro-6-phenyl-4H-s-triazolo-[4,3-a][1,5]benzodia-zepin-5-one |
| 62. | 2-methyl-propionic acid hydrazide | 1-isopropyl-8-chloro-6-phenyl-4H-s-triazolo-[4,3-a][1,5]benzodia-zepin-5-one |
| 63. | 1-cyanoacetic acid hydrazide | 1-cyanomethyl-8-chloro-6-phenyl-4H-s-triazolo-[4,3-a][1,5]benzodia-zepin-5-one |
| 64. | benzoic acid hydrazide | 1-phenyl-8-chloro-6-phenyl-4H-s-triazolo-[4,3-a][1,5]benzodia-zepin-5-one |

EXAMPLES 65–91

Following the procedure of Example 29, Method A, but substituting formic acid hydrazide for acetic acid hydrazide in Example 29, Method A, and the compounds indicated in Column I below for 7-chloro-5-phenyl-1H-1,5-benzodiazepin-4-one-2-thione in Example 29, Method A, the compounds indicated in Column II are obtained.

| | I | II |
|---|---|---|
| 65. | 5-phenyl-1H-1,5-benzodia-zepin-4-one-2-thione | 6-phenyl-4H-s-triazolo[4,3-a][1,5]-benzodiazepin-5-one |
| 66. | 7-(trifluoromethyl)-5-phenyl-1H-1,5-benzodia-zepin-4-one-2-thione | 8-(trifluoro-methyl)-6-phenyl-4H-s-triazolo[4,3-a][1,5]-benzodiazepin-5-one |
| 67. | 7-nitro-5-phenyl-1H-1,5-benzodiazepin-4-one-2-thione | 8-nitro-6-phenyl-4H-s-triazolo-[4,3-a][1,5]-benzodiazepin-5-one |
| 68. | 7-methyl-5-phenyl-1H-1,5-benzodiazepin-4-one-2-thione | 8-methyl-6-phenyl-4H-s-triazolo[4,3-a][1,5]-benzodiazepin-5-one |
| 69. | 7-methoxy-5-phenyl-1H-1,5-benzodiazepin-4-one-2-thione | 8-methoxy-6-phenyl-4H-s-triazolo[4,3-a][1,5]-benzodiazepin-5-one |
| 70. | 7-(methylthio)-5-phenyl-1H-1,5-benzodiazepin-4-one-2-thione | 8-(methylthio)-6-phenyl-4H-s-triazolo[4,3-a][1,5]-benzodiazepin-5-one |
| 71. | 7-pentyl-5-phenyl-1H-1,5-benzodiazepin-4-one-2-thione | 8-pentyl-6-phenyl-4H-s-triazolo[4,3-a][1,5]-benzodiazepin-5-one |
| 72. | 7-pentoxy-5-phenyl-1H-1,5-benzodiazepin-4-one-2-thione | 8-pentoxy-6-phenyl-4H-s-triazolo[4,3-a][1,5]-benzodiazepin-5-one |
| 73. | 7-bromo-5-phenyl-1H-1,5-benzodiazepin-4-one-2-thione | 8-bromo-6-phenyl-4H-s-triazolo[4,3-a][1,5]-benzodiazepin-5-one |
| 74. | 7-fluoro-5-phenyl-1H-1,5-benzodiazepin-4-one-2-thione | 8-fluoro-6-phenyl-4H-s-triazolo[4,3-a][1,5]-benzodiazepin-5-one |
| 75. | 7-cyano-5-phenyl-1H-1,5-benzodiazepin-4-one-2-thione | 8-cyano-6-phenyl-4H-s-triazolo[4,3-a][1,5]-benzodiazepin-5-one |
| 76. | 7-chloro-5-(2-chloro-phenyl)-1H-1,5-benzo-diazepin-4-one-2-thione | 8-chloro-6-(2-chloro-phenyl)-4H-s-triazolo-[4,3-a][1,5]benzodiazepin-5-one |
| 77. | 7-chloro-5-(2-fluoro-phenyl)-1H-1,5-benzo-diazepin-4-one-2-thione | 8-chloro-6-(2-fluoro-phenyl)-4H-s-triazolo-[4,3-a][1,5]benzodiazepin-5-one |
| 78. | 7-chloro-5-(3-chloro-phenyl)-1H-1,5-benzo-diazepin-4-one-2-thione | 8-chloro-6-(3-chloro-phenyl)-4H-s-triazolo-[4,3-a][1,5]benzodiazepin-5-one |
| 79. | 7-chloro-5-(4-chloro-phenyl)-1H-1,5-benzo-diazepine-4-one-2-thione | 8-chloro-6-(4-chloro-phenyl)-4H-s-triazolo-[4,3-a][1,5]benzodiazepin-5-one |
| 80. | 7-chloro-5-(2-methoxy-phenyl)-1H-1,5-benzo-diazepin-4-one-2-thione | 8-chloro-6-(2-methoxy-phenyl)-4H-s-triazolo-[4,3-a][1,5]benzodiazepin-5-one |
| 81. | 7-chloro-5-(3-methoxy-phenyl-1H-1,5-benzo-diazepin-4-one-2-thione | 8-chloro-6-(3-methoxy-phenyl)-4H-s-triazolo-[4,3-a][1,5]benzodiazepin-5-one |

| | I | II | III |
|---|---|---|---|
| 93. | benzylbromide | 7-(trifluoromethyl)-5-phenyl-1H-1,5-benzodiazepin-4-one-2-thione | 2-(benzylthio)-7-(trifluoromethyl)-5-phenyl-3H-1,5-benzodiazepin-4-one |
| 94. | O-propyl p-toluene-sulfonate | 7-nitro-5-(o-chlorophenyl)-1H-1,5-benzodiazepin-4-one-2-thione | 2-(propylthio)-7-nitro-5-(o-chlorophenyl)-3H-1,5-benzodiazepin-4-one |
| 95. | methyl iodide | 7-(trifluoromethyl)-5-phenyl-1H-1,5-benzodiazepin-4-one-2-thione | 2-(methylthio)-7-(trifluoromethyl)-5-phenyl-3H-1,5-benzodiazepin-4-one |
| 96. | dimethyl sulfate | 7-chloro-5-benzyl-1H-1,5-benzodiazepin-4-one-2-thione | 2-(methylthio)-7-chloro-5-benzyl-3H-1,5-benzodiazepin-4-one |

| | I | II |
|---|---|---|
| 82. | 7-chloro-5-(4-methoxyphenyl)-1H-1,5-benzodiazepin-4-one-2-thione | 8-chloro-6-(4-methoxyphenyl)-4H-s-triazolo[4,3-a][1,5]benzodiazepin-5-one |
| 83. | 7-chloro-5-(2-methylphenyl)-1H-1,5-benzodiazepin-4-one-2-thione | 8-chloro-6-(2-methylphenyl)-4H-s-triazolo[4,3-a][1,5]benzodiazepin-5-one |
| 84. | 7-chloro-5-(3-methylphenyl)-1H-1,5-benzodiazepin-4-one-2-thione | 8-chloro-6-(3-methylphenyl)-4H-s-triazolo[4,3-a][1,5]benzodiazepin-5-one |
| 85. | 7-chloro-5-(4-methylphenyl)-1H-1,5-benzodiazepin-4-one-2-thione | 8-chloro-6-(4-methylphenyl)-4H-s-triazolo[4,3-a][1,5]benzodiazepin-5-one |
| 86. | 3-methyl-7-chloro-5-phenyl-1H-1,5-benzodiazepin-4-one-2-thione | 4-methyl-8-chloro-6-phenyl-4H-s-triazolo[4,3-a][1,5]benzodiazepin-5-one |
| 87. | 3-(benzyloxy)-7-chloro-5-phenyl-1H-1,5-benzodiazepin-4-one-2-thione | 4-(benzyloxy)-8-chloro-6-phenyl-4H-s-triazolo[4,3-a][1,5]benzodiazepin-5-one |
| 88. | 3-methoxy-7-chloro-5-phenyl-1H-1,5-benzodiazepin-4-one-2-thione | 4-methoxy-8-chloro-6-phenyl-4H-s-triazolo[4,3-a][1,5]benzodiazepin-5-one |
| 89. | 8-methyl-5-phenyl-1H-1,5-benzodiazepin-4-one-2-thione | 9-methyl-6-phenyl-4H-s-triazolo[4,3-a][1,5]-benzodiazepin-5-one |
| 90. | 8-chloro-5-phenyl-1H-1,5-benzodiazepin-4-one-2-thione | 9-chloro-6-phenyl-4H-s-triazolo[4,3-a][1,5]-benzodiazepin-5-one |
| 91. | 8-(trifluoromethyl)-5-phenyl-1H-1,5-benzodiazepin-4-one-2-thione | 9-(trifluoromethyl)-6-phenyl-4H-s-triazolo[4,3-a][1,5]-benzodiazepin-5-one |

EXAMPLE 92

2-(Methylthio)-7-chloro-5-phenyl-3H-1,5-benzodiazepin-4-one

To 3.03 g of 7-chloro-5-phenyl-1H-1,5-benzodiazepin-4-one-2-thione in a solution of 0.40 g sodium hydroxide and 15 ml of methanol is added, with stirring a solution of 1.39 g of methyl iodide in 5 ml of methanol. Stirring is continued for 1 hour, the reaction is evaporated, diluted with 30 ml methylene chloride and filtered through a short Florisil column. After washing the column with ethyl acetate, the combined filtrates are evaporated to give the title compound.

EXAMPLES 93-96

Following the procedure of example 92 but substituting the compounds indicated in column I below for methyl iodide and the compounds indicated in column II for 7-chloro-5-phenyl-1H-1,5-benzodiazepin-4-one-2-thione in example 92, the benzodiazepinones indicated in column III are obtained.

EXAMPLES 97-102

Following the procedure of Example 92 but substituting the compounds indicated in Column I below for 7-chloro-5-phenyl-1H-1,5-benzodiazepin-4-one-2-thione in Example 92, the compounds indicated in Column II are obtained.

| | I | II |
|---|---|---|
| 97. | 5-phenyl-1H-1,5-benzodiazepin-4-one-2-thione | 2-(methylthio)-5-phenyl-3H-1,5-benzodiazepin-4-one |
| 98. | 7-(trifluoromethyl)-5-phenyl-1H-1,5-benzodiazepin-4-one-2-thione | 2-(methylthio)-7-(trifluoromethyl)-5-phenyl-3H-1,5-benzodiazepin-4-one |
| 99. | 7-nitro-5-phenyl-1H-1,5-benzodiazepin-4-one-2-thione | 2-(methylthio)-7-nitro-5-phenyl-3H-1,5-benzodiazepin-4-one |
| 100. | 7-methyl-5-phenyl-1H-1,5-benzodiazepin-4-one-2-thione | 2-(methylthio)-7-methyl-5-phenyl-3H-1,5-benzodiazepin-4-one |
| 101. | 7-methoxy-5-phenyl-1H-1,5-benzodiazepin-4-one-2-thione | 2-(-methylthio)-7-methoxy-5-phenyl-3H-1,5-benzodiazepin-4-one |
| 102. | 7-(methylthio)-5-phenyl-1H-1,5-benzodiazepin-4-one-2-thione | 2-(methylthio)-7-(methylthio)-5-phenyl-3H-1,5-benzodiazepin-4-one |

EXAMPLES 103-109

Following the procedure of Example 29, Method B, but substituting the compounds indicated in Column I below for acetic acid hydrazide in Example 29, Method B, the compounds indicated in Column II are obtained.

| | I | II |
|---|---|---|
| 103. | N,N-dimethylglycine-hydrazide | 1-[(Dimethylamino)-methyl]-8-chloro-6-phenyl-4H-s-triazolo[4,3-a][1,5]benzodiazepin-5-one |
| 104. | N,N-diethylglycine-hydrazide | 1-[(Diethylamino)-methyl]-8-chloro-6-phenyl-4H-s-triazolo[4,3-a][1,5]benzodiazepin-5-one |
| 105. | Pyrrolidinoacetic acid hydrazide | 1-[(1-Pyrrolidino)-methyl]-8-chloro-6-phenyl-4H-s-triazolo[4,3-a][1,5]benzodiazepin-5-one |
| 106. | 4-Morpholinoacetic acid hydrazide | 1-(4-Morpholinomethyl)-8-chloro-6-phenyl-4H- |

-continued

| | I | II |
|---|---|---|
| 107. | 1-Piperidinoacetic acid hydrazide | s-triazolo[4,3-a][1,5]-benzodiazepin-5-one 1-(1-Piperidinomethyl)-8-chloro-6-phenyl-4H-s-triazolo[4,3-a][1,5]-benzodiazepin-5-one |
| 108. | N-Methylglycine hydrazide | 1-[(Methylamino)-methyl]-8-chloro-6-phenyl-4H-s-triazolo[4,3-a][1,5]-benzodiazepin-5-one |
| 109. | 2-(p-Methoxybenzyloxy) acetic acid hydrazide | 1-[(p-Methoxybenzyloxy)-methyl]-8-chloro-6-phenyl-4H-s-triazolo-[4,3-a][1,5]benzodiazepin-5-one |

EXAMPLES 110–115

Following the procedure of Example 29, Method B, but substituting the compounds indicated in Column I below for acetic acid hydrazide and the compounds indicated in Column II below for 2-(methylthio)-7-chloro-5-phenyl-3H-1,5-benzodiazepin-4-one in Example 29, Method B, the compounds indicated in Column III are obtained.

| | I | II | III |
|---|---|---|---|
| 110. | formic acid hydrazide | 2-(methylthio)-7-chloro-5-benzyl-3H-1,5-benzodiazepin-4-one | 8-chloro-6-benzyl-4H-s-triazolo-[4,3-a][1,5]-benzodiazepin-5-one |
| 111. | acetic acid hydrazide | 2-(methylthio)-7-chloro-5-benzyl-3H-1,5-benzodiazepin-4-one | 1-methyl-8-chloro-6-benzyl-4H-s-triazolo[4,3-a][1,5]benzodiazepin-5-one |
| 112. | acetic acid hydrazide | 2-(benzylthio)-7-(trifluoromethyl)-5-phenyl-3H-1,5-benzodiazepin-4-one | 1-methyl-8-(trifluoromethyl)-6-phenyl-4H-s-triazolo[4,3-a][1,5]-benzodiazepin-5-one |
| 113. | acetic acid hydrazide | 2-(propylthio)-7-nitro-5-(o-chlorophenyl)-3H-1,5-benzodiazepin-4-one | 1-methyl-8-nitro-6-(o-chlorophenyl)-4H-s-triazolo[4,3-a]-[1,5]benzodiazepin-5-one |
| 114. | acetic acid hydrazide | 2-(methylthio)-7-(trifluoromethyl)-5-phenyl-3H-1,5-benzodiazepin-4-one | 1-methyl-8-(trifluoromethyl)-6-phenyl-4H-s-triazolo[4,3-a]-[1,5]benzodiazepin-5-one |
| 115. | acetic acid hydrazide | 2-(methylthio)-7-(trifluoromethyl)-5-benzyl-3H-1,5-benzodiazepin-4-one | 1-methyl-8-(trifluoromethyl)-6-benzyl-4H-s-triazolo[4,3-a][1,5]-benzodiazepin-5-one |

EXAMPLES 116–121

Following the procedure of Example 29, Method B, but substituting the compounds indicated in Column I below for 2-(methylthio)-7-chloro-5-phenyl-3H-1,5-benzodiazepin-4-one in Example 29, Method B, the compounds indicated in Column II are obtained.

| | I | II |
|---|---|---|
| 116. | 2-(methylthio)-5-phenyl 3H-1,5-benzodiazepin-4-one | 1-methyl-6-phenyl-4H-s-triazolo[4,3-a][1,5]-benzodiazepin-5-one |
| 117. | 2-(methylthio)-7-(trifluoromethyl)-5-phenyl-3H-1,5-benzodiazepin-4-one | 1-methyl-8-(trifluoromethyl)-6-phenyl-4H-s-triazolo-[4,3-a][1,5]benzodiazepin-5-one |
| 118. | 2-(methylthio)-7-nitro-5-phenyl-3H-1,5-benzodiazepin-4-one | 1-methyl-8-nitro-6-phenyl-4H-s-triazolo[4,3-a][1,5]-benzodiazepin-5-one |
| 119. | 2-(methylthio)-7-methyl-5-phenyl-3H-1,5-benzodiazepin-4-one | 1-methyl-8-methyl-6-phenyl-4H-s-triazolo[4,3-a][1,5]-benzodiazepin-5-one |
| 120. | 2-(methylthio)-7-methoxy-5-phenyl-3H-1,5-benzodiazepin-4-one | 1-methyl-8-methoxy-6-phenyl-4H-s-triazolo[4,3-a][1,5]-benzodiazepin-5-one |
| 121. | 2-(methylthio)-7-(methylthio)-5-phenyl-3H-1,5-benzodiazepin-4-one | 1-methyl-8-(methylthio)-6-phenyl-4H-s-triazolo[4,3-a]-[1,5]benzodiazepin-5-one |

EXAMPLE 122

1-(Hydroxymethyl)-8-chloro-6-phenyl-4H-s-triazolo-[4,3-a][1,5]benzodiazepin-5-one 3.1 g of 1-[(p-methoxybenzyloxy)-methyl]-8-chloro-6-phenyl-4H-s-triazolo[4,3-a][1,5]benzodiazepin-5-one in 30 ml acetic acid, at 25°, is stirred with 24 ml 48% aqueous hydrobromic acid for 20 minutes. The reaction is neutralized with 30% aqueous sodium hydroxide and extracted with chloroform. The organic phase is separated, washed with water, dried and the solvent evaporated to give the title compound.

EXAMPLE 123

1-(hydroxymethyl)-8-chloro-6-phenyl-4H-s-triazolo[4,3-a][1,5]benzodiazepin-5-one, methanesulfonate 3.4 g of 1-(hydroxymethyl)-8-chloro-6-phenyl-4H-s-triazolo[4,3-a][1,5]benzodiazepin-5-one in 30 ml chloroform is reacted with 3.03 g triethylamine and then 3.44 g methanesulfonyl chloride. The reaction is stirred at 20° for 90 minutes, washed with water, then with saturated aqueous sodium chloride and dried. The solvent is evaporated to give the title compound.

EXAMPLE 124

1-(Diethylaminomethyl)-8-chloro-6-phenyl-4H-s-triazolo[4,3-a][1,5]benzodiazepin-5-one 3.35 g of 1-(Hydroxymethyl)-8-chloro-6-phenyl-4H-s-triazolo[4,3-a][1,5]benzodiazepin-5-one, methanesulfonate in 15 ml dimethylsulfoxide at 0° is added dropwise with stirring to 3 ml of diethylamine in 10 ml dimethylsulfoxide. The reaction is stirred at 20° for 2 hours, diluted with methylene chloride, washed with water and then saturated aqueous sodium chloride. After drying, the solvent is evaporated to give the title compound.

EXAMPLES 125–132

Following the procedure of Example 124, but substituting the amines indicated in Column I below for diethylamine amine in Example 124, the compounds in Column II are obtained.

| | I | II |
|---|---|---|
| 125. | ammonia | 1-(aminomethyl)-8-chloro-6-phenyl-4H-s-triazolo-[4,3-a][1,5]benzodiazepin-5-one |
| 126. | methylamine | 1-(methylaminomethyl)-8-chloro-6-phenyl-4H-s-triazolo[4,3-a][1,5]-benzodiazepin-5-one |
| 127. | dimethylamine | 1-(dimethylaminomethyl)-8-chloro-6-phenyl-4H-s-triazolo[4,3-a][1,5]-benzodiazepin-5-one |
| 128. | pyrrolidine | 1-[(1-pyrrolidino)-methyl]-8-chloro-6-phenyl-4H-s-triazolo-[4,3-a][1,5]benzodiazepin-5-one |
| 129. | morpholine | 1-(4-morpholinomethyl)-8-chloro-6-phenyl-4H-s-triazolo[4,3-a][1,5]-benzodiazepin-5-one |
| 130. | 2-ethanolamine | 1-[[(2-hydroxyethyl)-amino]-methyl]-8-chloro-6-phenyl-4H-s-triazolo[4,3-a][1,5]-benzodiazepin-5-one |
| 131. | piperidine | 1-(piperidinomethyl)-8-chloro-6-phenyl-4H-s-triazolo[4,3-a][1,5]-benzodiazepin-5-one |
| 132. | benzylamine | 1-[(benzylamino)-methyl]-8-chloro-6-phenyl-4H-s-triazolo[4,3-a][1,5]-benzodiazepin-5-one |

EXAMPLE 133

2-Methoxy-7-chloro-5-phenyl-3H-1,5-benzodiazepin-4-one

To 11.4 g of 7-chloro-5-phenyl-1H-1,5-benzodiazepine-2,4-dione stirred in 150 ml methanol is added, dropwise, approximately 2.1 g of diazomethane in ether. After addition is complete, the reaction is stirred for 1 hour and filtered. The filtrate is evaporated and the residue diluted with a small amount of ether. The suspension is filtered and the filtrate evaporated to give the title compound.

EXAMPLE 134

1-[[(Benzyloxycarbonyl)-amino]-methyl]-8-chloro-6-phenyl-4H-s-triazolo[4,3-a][1,5]benzodiazepin-5-one 9.0 g of 2-methoxy-7-chloro-5-phenyl-3H-1,5-benzodiazepin-4-one and 6.69 g of 1-[(benzyloxycarbonyl)-amino]acetic acid hydrazide in 210 ml n-butanol and 50 ml dimethyl sulfoxide are heated at 140° for 9 hours. The reaction is evaporated and the residue is worked up as described in Example 29, Method D, to give the title compound.

EXAMPLE 135

1-(Aminomethyl)-8-chloro-6-phenyl-4H-s-triazolo[4,3-a]-[1,5]benzodiazepin-5-one 4.5 g of 1-[[(benzyloxycarbonyl)amino]-methyl]-8-chloro-6-phenyl-4H-s-triazolo[4,3-a][1,5]benzodiazepin-5-one in 60 ml acetic acid saturated with hydrogen bromide is stirred at 20° for 1 hour. The reaction mixture is concentrated to one-half its original volume in vacuo and diluted with ether. The precipitate is filtered off, suspended in methylene chloride and shaken with excess 2 N aqueous sodium bicarbonate. The organic phase is separated, washed with water, dried and evaporated to give the title compound.

EXAMPLE 136

1-(Acetoxymethyl)-8-chloro-6-phenyl-4H-s-triazolo-[4,3-a][1,5]benzodiazepin-5-one 3.4 g of 1-(hydroxymethyl)-8-chloro-6-phenyl-4H-s-triazolo[4,3-a][1,5]benzodiazepin-5-one and 1.0 g of acetic anhydride in 10 ml of pyridine are warmed in a steam bath for 0.2 hour and stirred at room temperature for 10 hours. The reaction mixture is cooled, diluted with 100 ml methylene chloride and washed with 100 ml water containing 0.84 g sodium bicarbonate. The organic phase is washed four times with water, dried and evaporated. The residue is triturated with a minimum amount of ether and the title compound filtered off, dried and recrystallized from methylene chloride and ether.

EXAMPLE 137

4-Acetoxy-8-chloro-6-phenyl-4H-triazolo[4,3-a][1,5]-benzodiazepin-5-one 6.2 g of 8-chloro-6-phenyl-4H-s-triazolo[4,3-a]-[1,5]benzodiazepin-5-one, 3 g of N-chlorosuccinimide and 0.1 g of azodiisobutyronitrile in 200 ml benzene are refluxed for 1 hour. The solvent is evaporated and the residue (which contains 4,8-dichloro-6-phenyl-4H-s-triazolo[4,3-a][1,5]benzodiazepin-5-one) is heated on a steam-bath for 10 minutes with 90 g of glacial acetic acid and 2.5 g of sodium acetate. The reaction is evaporated and the residue partitioned between chloroform and dilute aqueous sodium bicarbonate. The chloroform is washed with water, dried and the solvent evaporated to give the title compound.

EXAMPLE 138

4-Ethoxy-8-chloro-6-phenyl-4H-s-triazolo[4,3-a][1,5]-benzodiazepin-5-one

Following the procedure of Example 137 but substituting ethanol for both the glacial acetic acid and the sodium acetate in Example 137, the title compound is obtained.

EXAMPLE 139

4-Hydroxy-8-chloro-6-phenyl-4H-s-triazolo[4,3-a][1,5]-benzodiazepin-5-one 3.5 g of 4acetoxy-8-chloro-6-phenyl-4H-s-triazolo[4,3-a][1,4]benzodiazepin-5-one and 2.8 ml of 4 N aqueous sodium hydroxide in 160 ml of ethanol are stirred overnight at 25°. The reaction is neutralized with 0.5 g of acetic acid and the solvent is evaporated. The residue is partitioned between chloroform and water, the organic phase is dried and the solvent evaporated to give the title compound.

EXAMPLE 140

7-Chloro-5-benzyl-1H-1,5-benzodiazepine-2,4-dione

Method A

To a stirred refluxing solution of 22.3 g of 2-benzylamino-4-chloroaniline in 400 ml benzene is added, dropwise, a solution of 13.8 g of malonyl dichloride in 45 ml benzene. After addition is complete the reaction was refluxed for 7 hours, concentrated to ½ the original volume and cooled. The title compound is filtered off and dried. The filtrate is evaporated and the residue recrystallized from a mixture of ethanol-dimethylformamide to give additional product.

Method B 9.2 g of N-benzyl-N-(2'-amino-5'-chloro-phenyl)-malonamic acid, ethyl ester is added to a solution of 0.73 g of sodium in 100 ml ethanol. After refluxing for 2 hours the reaction is evaporated, the residue dissolved in water and acidified with hydroacetic acid. The title compound is filtered off and dried.

Method C 30 g of N-benzyl-N-(2'-nitro-5'-chloro-phenyl)-malonamic acid ethyl ester is added to a stirred suspension of 59 g iron powder, 360 ml of ethanol, 150 ml acetic acid and 105 ml water at reflux. After two hours, the reaction is filtered and the filtrate evaporated. The residue is treated with dilute aqueous ammonium hydroxide, extracted with methylene chloride, washed with water and dried. The solvent is evaporated and the residue treated with ethanolic potassium hydroxide. The ethanol is evaporated, the residue taken up in water and acidified to pH 6 with hydrochloric acid. The title compound is filtered off and dried.

Method D 11 g of N-benzyl-N-(2'-amino-5'-chloro-phenyl)-malonamic acid ethyl ester in 50 ml ethanol containing 1.7 g potassium hydroxide is kept at room temperature for 6 hours, refluxed for 45 minutes and the solvent evaporated. The residue is taken up in water, neutralized to pH 7 with hydrochloric acid and the title compound filtered off and dried.

EXAMPLES 141–151

Following the procedure of Example 140, Method A, but substituting the compounds indicated in Column I below for 2-benzylamino-4-chloroaniline in Example 140, Method A, the compounds in Column II are obtained.

| | I | II |
|---|---|---|
| 141. | 2-benzylamino-4-(trifluoromethyl)aniline | 7-(trifluoromethyl)-5-benzyl-1H-1,5-benzodiazepine-2,4-dione |
| 142. | 2-benzylamino-4-methylaniline | 7-methyl-5-benzyl-1H-1,5-benzodiazepine-2,4-dione |
| 143. | 2-benzylamino-aniline | 5-benzyl-1H-1,5-benzodiazepine-2,4-dione |
| 144. | 2-benzylamino-4-methoxyaniline | 7-methoxy-5-benzyl-1H-1,5-benzodiazepine-2,4-dione |
| 145. | 2-benzylamino-5-chloroaniline | 8-chloro-5-benzyl-1H-1,5-benzodiazepine-2,4-dione |
| 146. | 2-benzylamino-5-(trifluoromethyl)aniline | 8-(trifluoromethyl)-5-benzyl-1H-1,5-benzodiazepine-2,4-dione |
| 147. | 2-(p-methoxybenzylamino)-4-chloroaniline | 7-chloro-5-(p-methoxybenzyl)-1H-1,5-benzodiazepine-2,4-dione |
| 148. | 2-(p-methoxybenzylamino)-4-nitroaniline | 7-nitro-5-(p-methoxybenzyl)-1H-1,5-benzodiazepine-2,4-dione |
| 149. | 2-(p-methoxybenzylamino)-4-methoxyaniline | 7-methoxy-5-(p-methoxybenzyl)-1H-1,5-benzodiazepine-2,4-dione |
| 150. | 2-(p-methoxybenzylamino)-4-methylaniline | 7-methyl-5-(p-methoxybenzyl)-1H-1,5-benzodiazepine-2,4-dione |
| 151. | 2-(o,p-dimethoxybenzylamino)-4-(trifluoromethyl)methylaniline | 7-(trifluoromethyl)-5-(o,p-dimethoxybenzyl)-1H-1,5-benzodiazepine-2,4-dione |

EXAMPLES 152–164

Following the procedure of Example 1 but substituting the compounds indicated in Column 1 below for 7-chloro-5-phenyl-1H-1,5-benzodiazepine-2,4-dione in Example 1, the compounds indicated in Column II are obtained.

| | I | II |
|---|---|---|
| 152. | 5-benzyl-1H-1,5-benzodiazepine-2,4-dione | 5-benzyl-1H-1,5-benzodiazepin-4-one-2-thione |
| 153. | 7-chloro-5-benzyl-1H-1,5-benzodiazepine-2,4-dione | 7-chloro-5-benzyl-1H-1,5-benzodiazepin-4-one-2-thione |
| 154. | 7-methyl-5-benzyl-1H-1,5-benzodiazepine-2,4-dione | 7-methyl-5-benzyl-1H-1,5-benzodiazepin-4-one-2-thione |
| 155. | 7-methoxy-5-benzyl-1H-1,5-benzodiazepine-2,4-dione | 7-methoxy-5-benzyl-1H-1,5-benzodiazepin-4-one-2-thione |
| 156. | 8-(trifluoromethyl)-5-benzyl-1H-1,5-benzodiazepine-2,4-dione | 8-(trifluoromethyl)-5-benzyl-1H-1,5-benzodiazepin-4-one-2-thione |
| 157. | 8-chloro-5-benzyl-1H-1,5-benzodiazepine-2,4-dione | 8-chloro-5-benzyl-1H-1,5-benzodiazepin-4-one-2-thione |
| 158. | 7-(trifluoromethyl)-5-benzyl-1H-1,5-benzodiazepine-2,4-dione | 7-(trifluoromethyl)-5-benzyl-1H-1,5-benzodiazepin-4-one-2-thione |
| 159. | 7-chloro-5-(p-methoxybenzyl)-1H-1,5-benzodiazepine-2,4-dione | 7-chloro-5-(p-methoxybenzyl)-1H-1,5-benzodiazepin-4-one-2-thione |
| 160. | 7-nitro-5-(p-methoxybenzyl)-1H-1,5-benzodiazepine-2,4-dione | 7-nitro-5-(p-methoxybenzyl)-1H-1,5-benzodiazepin-4-one-2-thione |
| 161. | 7-methoxy-5-(p-methoxybenzyl)-1H-1,5-benzodiazepine-2,4-dione | 7-methoxy-5-(p-methoxybenzyl)-1H-1,5-benzodiazepin-4-one-2-thione |
| 162. | 7-methyl-5-(p-methoxybenzyl)-1H-1,5-benzodiazepine-2,4-dione | 7-methyl-5-(p-methoxybenzyl)-1H-1,5-benzodiazepin-4-one-2-thione |
| 163. | 7-(trifluoromethyl)-5-(p-methoxybenzyl)-1H-1,5-benzodiazepine-2,4-dione | 7-(trifluoromethyl)-5-(p-methoxybenzyl)-1H-1,5-benzodiazepin-4-one-2-thione |
| 164. | 7-(trifluoromethyl)-5-(o,p-dimethoxybenzyl)-1H-1,5-benzodiazepine-2,4-dione | 7-(trifluoromethyl)-5-(o,p-dimethoxybenzyl)-1H-1,5-benzodiazepin-4-one-2-thione |

EXAMPLES 165–177

Following the procedure of Example 29, Method A, but substituting the compounds indicated in Column I below for 7-chloro-5-phenyl-1H-1,5-benzodiazepin-4-one-2-thione in Example 29, Method A, the compounds indicated in Column II are obtained.

| | I | II |
|---|---|---|
| 165. | 5-benzyl-1H-1,5-benzodiazepin-4-one-2-thione | 1-methyl-6-benzyl-4H-s-triazolo[4,3-a][1,5]-benzodiazepin-5-one |
| 166. | 7-chloro-5-benzyl-1H-1,5-benzodiazepin-4-one-2-thione | 1-methyl-8-chloro-6-benzyl-4H-s-triazolo[4,3-a][1,5]benzodiazepin-5-one |

| | I | II |
|---|---|---|
| 167. | 7-methyl-5-benzyl-1H-1,5-benzodiazepin-4-one-2-thione | 1-methyl-8-methyl-6-benzyl-4H-s-triazolo[4,3-a][1,5]benzodiazepin-5-one |
| 168. | 7-methoxy-5-benzyl-1H-1,5-benzodiazepin-4-one-2-thione | 1-methyl-8-methoxy-6-benzyl-4H-s-triazolo[4,3-a][1,5]benzodiazepin-5-one |
| 169. | 8-(trifluoromethyl)-5-benzyl-1H-1,5-benzodiazepin-4-one-2-thione | 1-methyl-9-(trifluoromethyl)-6-benzyl-4H-s-triazolo[4,3-a][1,5]benzodiazepin-5-one |
| 170. | 8-chloro-5-benzyl-1H-1,5-benzodiazepin-4-one-2-thione | 1-methyl-9-chloro-6-benzyl-4H-s-triazolo[4,3-][1,5]benzodiazepin-5-one |
| 171. | 7-(trifluoromethyl)-5-benzyl-1H-1,5-benzodiazepin-4-one-2-thione | 1-methyl-8-(trifluoromethyl)-6-benzyl-4H-s-triazolo[4,3-a][1,5]benzodiazepin-5-one |
| 172. | 7-chloro-5-(p-methoxybenzyl)-1H-1,5-benzodiazepin-4-one-2-thione | 1-methyl-8-chloro-6-(p-methoxybenzyl)-4H-s-triazolo[4,3-a][1,5]benzodiazepin-5-one |
| 173. | 7-nitro-5-(p-methoxybenzyl)-1H-1,5-benzodiazepin-4-one-2-thione | 1-methyl-8-nitro-6-(p-methoxybenzyl)-4H-s-triazolo[4,3-a][1,5]benzodiazepin-5-one |
| 174. | 7-methoxy-5-(p-methoxybenzyl)-1H-1,5-benzodiazepin-4-one-2-thione | 1-methyl-8-methoxy-6-(p-methoxybenzyl)-4H-s-triazolo[4,3-a][1,5]benzodiazepin-5-one |
| 175. | 7-methyl-5-(p-methoxybenzyl)-1H-1,5-benzodiazepin-4-one-2-thione | 1-methyl-8-methyl-6-(p-methoxybenzyl)-4H-s-triazolo[4,3-a][1,5]benzodiazepin-5-one |
| 176. | 7-(trifluoromethyl)-5-(p-methoxybenzyl)-1H-1,5-benzodiazepin-4-one-2-thione | 1-methyl-8-(trifluoromethyl)-6-(p-methoxybenzyl)-4H-s-triazolo[4,3-a][1,5]benzodiazepin-5-one |
| 177. | 7-(trifluoromethyl)-5-(o,p-dimethoxybenzyl)-1H-1,5-benzodiazepin-4-one-2-thione | 1-methyl-8-(trifluoromethyl)-6-(o,p-dimethoxybenzyl)-4H-s-triazolo[4,3-a][1,5]benzodiazepin-5-one |

EXAMPLES 178–189

Following the procedure of Example 29, Method A, but substituting the acid hydrazides indicated in Column I below for acetic acid hydrazide and the compounds indicated in column II below for 7-chloro-5-phenyl-1H-1,5-benzodiazepin-4-one-2-thione in Example 29, Method A, the compounds in Column III are obtained:

| | I | II | III |
|---|---|---|---|
| 178. | formic acid hydrazide | 7-chloro-5-benzyl-1H-1,5-benzodiazepin-4-one-2-thione | 8-chloro-6-benzyl-4H-s-triazolo[4,3-a][1,5]benzodiazepin-5-one |
| 179. | propionic acid hydrazide | 7-chloro-5-benzyl-1H-1,5-benzodiazepin-4-one-2-thione | 1-ethyl-8-chloro-6-benzyl-4H-s-triazolo[4,3-a][1,5]benzodiazepin-5-one |
| 180. | cyclopropane carboxylic acid hydrazide | 7-chloro-5-benzyl-1H-1,5-benzodiazepin-4-one-2-thione | 1-cyclopropyl-8-chloro-6-benzyl-4H-s-triazolo[4,3-a][1,5]benzodiazepin-5-one |
| 181. | N,N-dimethylaminoglycine hydrazide | 7-chloro-5-benzyl-1H-1,5-benzodiazepin-4-one-2-thione | 1-[(dimethylamino)methyl]-8-chloro-6-benzyl-4H-s-triazolo[4,3-a][1,5]benzodiazepin-5-one |
| 182. | formic acid hydrazide | 7-(trifluoromethyl)-5-(p-methoxybenzyl)-1H-1,5-benzodiazepin-4-one-2-thione | 8-(trifluoromethyl)-6-(p-methoxybenzyl)-4H-s-triazolo[4,3-a][1,5]benzodiazepin-5-one |
| 183. | propionic acid hydrazide | 7-(trifluoromethyl)-5-(p-methoxybenzyl)-1H-1,5-benzodiazepin-4-one-2-thione | 1-ethyl-8-(trifluoromethyl)-6-(p-methoxybenzyl)-4H-s-triazolo[4,3-a][1,5]benzodiazepin-5-one |
| 184. | cyclopropane carboxylic acid hydrazide | 7-(trifluoromethyl)-5-(p-methoxybenzyl)-1H-1,5-benzodiazepin-4-one-2-thione | 1-cyclopropyl-8-(trifluoromethyl)-6-(p-methoxybenzyl)-4H-s-triazolo[4,3-a][1,5]benzodiazepin-5-one |
| 185. | N,N-dimethylaminoglycine hydrazide | 7-(trifluoromethyl)-5-(p-methoxybenzyl)-1H-1,5-benzodiazepin-4-one-2-thione | 1-[(dimethylamino)methyl]-8-(trifluoromethyl)-6-(p-methoxybenzyl)-4H-s-triazolo[4,3-a][1,5]benzodiazepin-5-one |
| 186. | formic acid hydrazide | 7-nitro-5-(p-methoxybenzyl)-1H-1,5-benzodiazepin-4-one-2-thione | 8-nitro-6-(p-methoxybenzyl)-4H-s-triazolo[4,3-a][1,5]benzodiazepin-5-one |
| 187. | propionic acid hydrazide | 7-nitro-5-(p-methoxybenzyl)-1H-1,5-benzodiazepin-4-one-2-thione | 1-ethyl-8-nitro-6-(p-methoxybenzyl)-4H-s-triazolo[4,3-a][1,5]benzodiazepin-5-one |
| 188. | cyclopropane carboxylic acid hydrazide | 7-nitro-5-(p-methoxybenzyl)-1H-1,5-benzodiazepin-4-one-2-thione | 1-cyclopropyl-8-nitro-6-(p-methoxybenzyl)-4H-s-triazolo[4,3-a][1,5]benzodiazepin-5-one |
| 189. | N,N-dimethylaminoglycine hydrazide | 7-nitro-5-(p-methoxybenzyl)-1H-1,5-benzodiazepin-4-one-2-thione | 1-[(dimethylamino)methyl]-8-nitro-6-(p-methoxybenzyl)-4H-s-triazolo[4,3-a][1,5]benzodiazepin-5-one |

EXAMPLE 190

8-Chloro-4H-s-triazolo[4,3-a][1,5]benzodiazepin-5-one

Method A 2.92 g of 8-chloro-6-benzyl-4H-s-triazolo[4,3-a][1,5]benzodiazepin-5-one in 300 ml acetic acid containing 0.3 g of pre-reduced Raney nickel catalyst is hydrogenated at 60° starting with an initial hydrogen pressure of 60 p.s.i. The reduction is stopped after 0.01 mole of hydrogen has been absorbed, the catalyst filtered off and the solvent evaporated. The residue is stirred with water and the title compound is filtered off and dried.

Method B 2.92 g of 8-chloro-6-(p-methoxybenzyl)-4H-s-triazolo[4,3-a][1,5]benzodiazepin-5-one in 100 ml of anhydrous hydrogen fluoride is stirred at 20° C. for one hour. The hydrogen fluoride is then evaporated; the residue is partitioned between methylene chloride and dilute aqueous sodium bicarbonate. The organic phase is washed with water, dried and evaporated. The residue is stirred with ether and the title compound is filtered off and dried.

EXAMPLES 191–201

Following the procedure of Example 190, Method A, but substituting the compounds indicated in Column I below for 8-chloro-6-benzyl-4H-s-triazolo[4,3-a][1,5]benzodiazepin-5-one in Example 190, Method A, the compounds indicated in Column II are obtained.

| | I | II |
|---|---|---|
| 191. | 1-methyl-6-benzyl-4H-s-triazolo[4,3-a][1,5]benzodiazepin-5-one | 1-methyl-4H-s-triazolo[4,3-a][1,5]benzodiazepin-5-one |
| 192. | 1-methyl-8-chloro-6-benzyl-4H-s-triazolo[4,3-a][1,5]benzodiazepin-5-one | 1-methyl-8-chloro-4H-s-triazolo[4,3-a][1,5]benzodiazepin-5-one |
| 193. | 1-methyl-8-methyl-6-benzyl-4H-s-triazolo[4,3-a][1,5]benzodiazepin-5-one | 1-methyl-8-methyl-4H-s-triazolo[4,3-a][1,5]benzodiazepin-5-one |
| 194. | 1-methyl-8-methoxy-6-benzyl-4H-s-triazolo-4,3-a][1,5]benzodiazepin-5-one | 1-methyl-8-methoxy-4H-s-triazolo[4,3-a][1,5]benzodiazepin-5-one |
| 195. | 1-methyl-9-(trifluoromethyl)-6-benzyl-4H-s-triazolo[4,3-a][1,5]benzodiazepin-5-one | 1-methyl-9-(trifluoromethyl)-4H-s-triazolo[4,3-a][1,5]benzodiazepin-5-one |
| 196. | 1-methyl-9-chloro-6-benzyl-4H-s-triazolo[4,3-a][1,5]benzodiazepin-5-one | 1-methyl-9-chloro-4H-s-triazolo[4,3-a][1,5]benzodiazepin-5-one |
| 197. | 1-methyl-8-(trifluoromethyl)-6-benzyl-4H-s-triazolo[4,3-a][1,5]benzodiazepin-5-one | 1-methyl-8-(trifluoromethyl)-4H-s-triazolo[4,3-a][1,5]benzodiazepin-5-one |
| 198. | 8-chloro-6-benzyl-4H-s-triazolo[4,3-a][1,5]benzodiazepin-5-one | 8-chloro-4H-s-triazolo[4,3-a][1,5]benzodiazepin-5-one |
| 199. | 1-ethyl-8-chloro-6-benzyl-4H-s-triazolo[4,3-a][1,5]benzodiazepin-5-one | 1-ethyl-8-chloro-4H-s-triazolo[4,3-a][1,5]benzodiazepin-5-one |
| 200. | 1-cyclopropyl-8-chloro-6-benzyl-4H-s-triazolo[4,3-a][1,5]benzodiazepin-5-one | 1-cyclopropyl-8-chloro-4H-s-triazolol[4,3-a][1,5]benzodiazepin-5-one |
| 201. | 1-[(dimethylamino)methyl]-8-chloro-6-benzyl-4H-s-triazolo[4,3-a][1,5]benzodiazepin-5-one | 1-[(dimethylamino)methyl]-8-chloro-4H-s-triazolo[4,3-a][1,5]benzodiazepin-5-one |

EXAMPLES 202–215

Following the procedure of Example 190, Method B, but substituting the compounds indicated in Column I below for 8-chloro-6-(p-methoxybenzyl)-4H-s-triazolo[4,3-a][1,5]benzodiazepin-5-one in Examples 190, Method B, the compounds indicated in Column II are obtained.

| | I | II |
|---|---|---|
| 202. | 8-(trifluoromethyl)-6-(p-methoxybenzyl)-4H-s-triazolo[4,3-a][1.5]-benzodiazepin-5-one | 8-(trifluoromethyl)-4H-s-triazolo[4,3-a][1.5]-benzodiazepin-5-one |
| 203. | 1-ethyl-8-(trifluoromethyl)-6-(p-methoxybenzyl)-4H-s-triazolo[4,3-a][1,5]benzodiazepin-5-one | 1-ethyl-8-(trifluoromethyl)-4H-s-triazolo[4,3-a][1,5]benzodiazepin-5-one |
| 204. | 1-cyclopropyl-8-(trifluoromethyl)-6-(p-methoxybenzyl)-4H-s-triazolo[4,3-a][1,5]-benzodiazepin-5-one | 1-cyclopropyl-8-(trifluoromethyl)-4H-s-triazolo[4,3-a][1,5]-benzodiazepin-5-one |
| 205. | 1-[(dimethylamino)methyl]-8-(trifluoromethyl)-6-(p-methoxybenzyl-4H-s-triazolo[4,3-a][1,5]benzodiazepin-5-one | 1-[(dimethylamino)methyl]-8-(trifluoromethyl-4H-s-triazolo[4,3-a][1,5]benzodiazepin-5-one |
| 206. | 8-nitro-6-(p-methoxybenzyl)-4H-s-triazolo[4,3-a][1,5]benzodiazepin-5-one | 8-nitro-4H-s-triazolo[4,3-a][1,5]benzodiazepin-5-one |
| 207. | 1-ethyl-8-nitro-6-(p-methoxybenzyl)-4H-s-triazolo[4,3-a][1,5]benzodiazepin-5-one | 1-ethyl-8-nitro-4H-s-triazolo[4,3-a][1,5]benzodiazepin-5-one |
| 208. | 1-cyclopropyl-8-nitro-6-(p-methoxybenzyl)-4H-s-triazolo[4,3-a]-[1,5]benzodiazepin-5-one | 1-cyclopropyl-8-nitro-4H-s-triazolo[4,3-a]-[1,5]benzodiazepin-5-one |
| 209. | 1-[(dimethylamino)methyl]-8-nitro-6-(p-methoxybenzyl)-4H-s-triazolo[4,3-a][1,5]-benzodiazepin-5-one | 1-[(dimethylamino)methyl]-8-nitro-4H-s-triazolo[4,3-a][1,5]benzodiazepin-5-one |
| 210. | 1-methyl-8-chloro-6-(p-methoxybenzyl)-4H-s-triazolo[4,3-a][1,5]benzodiazepin-5-one | 1-methyl-8-chloro-4H-s-triazolo[4,3-a][1,5]-benzodiazepin-5-one |
| 211. | 1-methyl-8-nitro-6-(p-methoxybenzyl)-4H-s-triazolo[4,3-a][1,5]benzodiazepin-5-one | 1-methyl-8-nitro-4H-s-triazolo[4,3-a][1,5]-benzodiazepin-5-one |
| 212. | 1-methyl-8-methoxy-6-(p-methoxybenzyl)-4H-s-triazolo[4,3-a][1,5]benzodiazepin-5-one | 1-methyl-8-methoxy-4H-s-triazolo[4,3-a]-[1,5]benzodiazepin-5-one |
| 213. | 1-methyl-8-methyl-6-(p-methoxybenzyl)-4H-s-triazolo[4,3-a][1,5]benzodiazepin-5-one | 1-methyl-8-methyl-4H-s-triazolo[4,3-a]-[1,5]benzodiazepin-5-one |
| 214. | 1-methyl-8-(trifluoromethyl)-6-(p-methoxybenzyl)-4H-s-triazolo[4,3-a][1,5]benzodiazepin-5-one | 1-methyl-8-(trifluoromethyl)-4H-s-triazolo[4,3-a][1,5]benzodiazepin-5-one |
| 215. | 1-methyl-8-(trifluoromethyl)-6-(o,p-dimethoxybenzyl)-4H-s-triazolo[4,3-a][1,5]benzodiazepin-5-one | 1-methyl-8-(trifluoromethyl)-4H-s-triazolo[4,3-a][1,5]benzodiazepin-5-one |

EXAMPLES 216–235

Following the procedure of Example 29, Methods C or I, but substituting the compounds indicated in Column I below for 1-methyl-8-chloro-4H-s-triazolo-[4,3-a][1,5]benzodiazepin-5-one in Example 29, Methods C or I, the compounds indicated in Column II are obtained.

| | I | II |
|---|---|---|
| 216. | 1-methyl-4H-s-triazolo-[4,3-a][1,5]benzodiazepin-5-one | 1-methyl-6-phenyl-4H-s-triazolo[4,3-a][1,5]-benzodiazepin-5-one |
| 217. | 1-methyl-8-chloro-4H-s-triazolo[4,3-a][1,5]-benzodiazepin-5-one | 1-methyl-8-chloro-6-phenyl-4H-s-triazolo-[4,3-a][1,5]benzodiazepin-5-one |
| 218. | 1-methyl-8-methoxy-4H-s-triazolo[4,3-a][1,5]-benzodiazepin-5-one | 1-methyl-8-methoxy-6-phenyl-4H-s-triazolo-[4,3-a][1,5]benzodiazepin-5-one |
| 219. | 1-methyl-8-trifluoromethyl)-4H-s-triazolo-[4,3-a][1,5]benzodiazepin-5-one | 1-methyl-8-(trifluoromethyl)-6-phenyl-4H-s-triazolo[4,3-a][1,5]-benzodiazepin-5-one |
| 220. | 1-methyl-8-nitro-4H-s-triazolo[4,3-a][1,5]-benzodiazepin-5-one | 1-methyl-8-nitro-6-phenyl-4H-s-triazolo[4,3-a][1,5]-benzodiazepin-5-one |
| 221. | 1-methyl-9-chloro-4H-s-triazolo[4,3-a]-[1,5]benzodiazepin-5-one | 1-methyl-9-chloro-6-phenyl-4H-s-triazolo-[4,3-a][1,5]benzodiazepin-5-one |
| 222. | 1-methyl-9-(trifluoromethyl)-4H-s-triazolo[4,3-a][1,5]benzodiazepin-5-one | 1-methyl-9-(trifluoromethyl)-6-phenyl-4H-s-triazolo[4,3-a]-[1,5]benzodiazepin-5-one |
| 223. | 1,8-dimethyl-4H-s-triazolo[4,3-a][1,5]-benzodiazepin-5-one | 1,8-dimethyl-6-phenyl-4H-s-triazolo[4,3-a]-[1,5]benzodiazepin-5-one |
| 224. | 8-(trifluoromethyl)-4H-s-triazolo[4,3-a][1,5]-benzodiazepin-5-one | 8-(trifluoromethyl)-6-phenyl-4H-s-triazolo-[4,3-a][1,5]benzodiazepin-5-one |
| 225. | 1-ethyl-8-(trifluoromethyl)-4H-s-triazolo-[4,3-a][1,5]benzodiazepin-5-one | 1-ethyl-8-(trifluoromethyl)-6-phenyl-4H-s-triazolo[4,3-a][1,5]-benzodiazepin-5-one |
| 226. | 1-cyclopropyl-8-(trifluoromethyl)-4H-s-triazolo[4,3-a][1,5]-benzodiazepin-5-one | 1-cyclopropyl-8-(trifluoromethyl)-6-phenyl-4H-s-triazolo[4,3-a]-[1,5]benzodiazepin-5-one |
| 227. | 1-[(dimethylamino)-methyl]-8-(trifluoromethyl)-4H-s-triazolo-[4,3-a][1,5]benzo-diazepin-5-one | 1-[(dimethylamino)-methyl]-8-(trifluoromethyl)-6-phenyl-4H-s-triazolo[4,3-a][1,5]-benzodiazepin-5-one |
| 228. | 8-nitro-4H-s-triazolo-[4,3-a][1,5]benzodiazepin-5-one | 8-nitro-6-phenyl-4H-s-triazolo[4,3-a]-[1,5]benzodiazepin-5-one |
| 229. | 1-ethyl-8-nitro-4H-s-triazolo[4,3-a]-[1,5]benzodiazepin-5-one | 1-ethyl-8-nitro-6-phenyl-4H-triazolo-[4,3-a][1,5]benzodiazepin-5-one |
| 230. | 1-cyclopropyl-8-nitro-4H-s-triazolo[4,3-a]-[1,5]benzodiazepin-5-one | 1-cyclopropyl-8-nitro-6-phenyl-4H-triazolo-[4,3-a][1,5]benzodiazepin-5-one |
| 231. | 1-[(dimethylamino)-methyl]-8-nitro-4H-s-triazolo[4,3-a]-[1,5]benzodiazepin-5-one | 1-[(dimethylamino)-methyl]-8-nitro-6-phenyl-4H-s-triazolo-[4,3-a][1,5]benzodiazepin-5-one |
| 232. | 8-chloro-4H-s-triazolo[4,3-a][1,5]-benzodiazepin-5-one | 8-chloro-6-phenyl-4H-s-triazolo[4,3-a]-[1,5]benzodiazepin-5-one |
| 233. | 1-ethyl-8-chloro-4H-s-triazolo[4,3-a]-[1,5]benzodiazepin-5-one | 1-ethyl-8-chloro-6-phenyl-4H-s-triazolo[4,3-a]-[1,5]benzodiazepin-5-one |
| 234. | 1-cyclopropyl-8-chloro-4H-s-triazolo-[4,3-a][1,5]benzodiazepin-5-one | 1-cyclopropyl-8-chloro-6-phenyl-4H-s-triazolo-[4,3-a][1,5]benzodiazepin-5-one |
| 235. | 1-[(dimethylamino)-methyl]-8-chloro-4H-s-triazolo[4,3-a]-5-one | 1-[(dimethylamino)-methyl]-8-chloro-6-phenyl-4H-s-triazolo-[4,3-a][1,5]benzodiazepin-5-one |

EXAMPLE 236

1-Methyl-8-chloro-6-(o-chlorophenyl)-4H-s-triazolo-[4,3-a][1,5]benzodiazepin-5-one To a stirred mixture of 12.4 g of 1-methyl-8-chloro-4H-s-triazolo[4,3-a][1,5]benzodiazepin-5-one, 5 g of copper powder and 1 g of cupric sulfate in 100 ml of o-chlorobromobenzene at 90° C., was added, portionwise over a 30 minute period, 4.5 g of potassium acetate. The reaction is heated at 165° C. for 9 hours and then worked up as described in Example 29, Method C, to give the title compound.

EXAMPLES 237–243

Following the procedure of Example 236 but substituting the compounds indicated in Column I below for 1-methyl-8-chloro-4H-s-triazolo[4,3-a][1,5]benzodiazepin-5-one in Example 236, the compounds indicated in Column II are obtained.

| | I | II |
|---|---|---|
| 237. | 1-methyl-4H-s-triazolo-[4,3-a][1,5]benzodiazepin-5-one | 1-methyl-6-(o-chlorophenyl)-4H-s-triazolo-[4,3-a][1,5]benzodiazepin-5-one |
| 238. | 1-methyl-8-chloro-4H-s-triazolo[4,3-a][1,5]-benzodiazepin-5-one | 1-methyl-8-chloro-6-(o-chlorophenyl)-4H-s-triazolo[4,3-a][1,5]-benzodiazepin-5-one |
| 239. | 1-methyl-8-methoxy-4H-s-triazolo[4,3-a][1,5]-benzodiazepin-5-one | 1-methyl-8-methoxy-6-(o-chlorophenyl-4H-s-triazolo[4,3-a][1,5]-benzodiazepin-5-one |
| 240. | 1-methyl-8-(trifluoromethyl)-4H-s-triazolo-[4,3-a][1,5]benzodiazepin-5-one | 1-methyl-8-(trifluoromethyl)-6-(o-chlorophenyl)-4H-s-triazolo-[4,3-a][1,5]benzodiazepin-5-one |
| 241. | 1-methyl-8-nitro-4H-s-triazolo[4,3-a]-[1,5]benzodiazepin-5-one | 1-methyl-8-nitro-6-(o-chlorophenyl)-4H-s-triazolo[4,3-a]-[1,5]benzodiazepin-5-one |
| 242. | 1-methyl-9-chloro-4H-s-triazolo[4,3-a]-[1,5]benzodiazepin-5-one | 1-methyl-9-chloro-6-(o-chlorophenyl)-4H-s-triazolo[4,3-a][1,5]-benzodiazepin-5-one |
| 243. | 1-methyl-9-trifluoromethyl)-4H-s-triazolo-[4,3-a][1,5]benzodiazepin-5-one | 1-methyl-9-(trifluoromethyl)-6-(o-chlorophenyl)-4H-s-triazolo-[4,3-a][1,5]benzodiazepin-5-one |
| 244. | 1,8-dimethyl-4H-s-triazolo[4,3-a][1,5]-benzodiazepin-5-one | 1,8-dimethyl-6-(o-chlorophenyl)-4H-s-triazolo-[4,3-a][1,5]benzodiazepin-5-one |

EXAMPLE 245

N-Benzyl-N-(2'-nitro-5'-chlorophenyl)malonamic acid, ethyl ester 52 g of N-benzyl-N-(2-nitro-5-chlorophenyl) amine and 35.5 g of (chloroformyl)acetic acid ethyl ester in 500 ml benzene are refluxed for 15 hours. The reaction is cooled, washed with dilute aqueous sodium bicarbonate, dried and the solvent evaporated to give the title compound.

EXAMPLES 246–252

Following the procedure of Example 245, but substituting the compounds indicated in Column I below for N-benzyl-N-(2-nitro-5-chlorophenyl)amine in Example 245, the compounds indicated in Column II are obtained.

| I | II |
|---|---|
| 246. N-benzyl-N-[2-nitro-5-trifluoromethyl-phenyl amine | N-benzyl-N-[2'-nitro-5'-(trifluoromethyl)]-malonamic acid ethyl ester |
| 247. N-benzyl-N-(2-nitro-5-methylphenyl)amine | N-benzyl-N-(2'-nitro-5'-methylphenyl)malonamic acid ethyl ester |
| 248. N-benzyl-N-(2-nitro-5-methoxyphenyl)amine | N-benzyl-N-(2'-nitro-5'-methoxyphenyl)malonamic acid ethyl ester |
| 249. N-benzyl-N-(2-nitro-phenyl)amine | N-benzyl-N-(2'-nitro-phenyl(malonamic acid ethyl ester |
| 250. N-benzyl-N-(2'-nitro-4-chlorophenyl)amine | N-benzyl-N-(2'-nitro-4'-chlorophenyl) malonamic acid, ethyl ester |
| 251. N-(4-methoxybenzyl)-N-(2-nitro-5-chlorophenyl)amine | N-(4-methoxybenzyl)-N-(2'-nitro-5'-chlorophenyl)malonamic acid ethyl ester |
| 252. N-(4-methoxybenzyl)-N-[2-nitro-5-(trifluoromethyl)phenyl]amine | N-(4-methoxybenzyl)-N-[2'-nitro-5'-(trifluoromethyl)phenyl]-malonamic acid, ethyl ester |

EXAMPLES 253–256

Following the procedure of Example 245 but substituting the compounds indicated in column I below for (chloroformyl)acetic acid ethyl ester in example 245, the compounds indicated in column II are obtained.

| I | I |
|---|---|
| 253. chloroformyl)acetic acid methyl ester | N-benzyl-N-(2'-nitro-5'-chlorophenyl)malonamic acid methyl ester |
| 254. (chloroformyl)acetic acid butyl ester | N-benzyl-N-(2'-nitro-5'-chlorophenyl)malonamic acid butyl ester |
| 255. (chloroformyl)acetic acid phenyl ester | N-benzyl-N-(2'-nitro-5'-chlorophenyl)malonamic acid phenyl ester |
| 256. (chloroformyl)acetic acid (p-methylphenyl) ester | N-benzyl-N-(2'-nitro-5'-chlorophenyl)malonamic acid (p-methylphenyl)-ester |

EXAMPLE 257

N-Benzyl-N-(2'-amino-5'-chlorophenyl)malonamic acid ethyl ester

Method A 37.6 g of N-benzyl-N-(2'-nitro-5'-chlorophenyl)-malonamic acid ethyl ester and 0.5 g 10% palladium-on-carbon in 200 ml ethanol containing 0.2 moles of hydrogen chloride are hydrogenated on a Parr shaker, with cooling, at ambient temperature. The reaction is stopped after 0.3 moles of hydrogen are absorbed or when hydrogen uptake ceases, whichever comes first. The reaction is diluted with chloroform, filtered and the filtrate evaporated. The residue is suspended in methylene chloride and shaken with excess aqueous sodium bicarbonate. The organic phase is washed with water, dried and evaporation to give the title compound.

Method B

Following the procedure of Example 257, Method A, but substituting Raney nickel and methanol for the 10% palladium-on-carbon and ethanolic hydrogen chloride, respectively, in Example 257, Method A, and running the reaction at an initial hydrogen pressure of 3 atm., gives the title compound.

EXAMPLES 258–268

Following the procedure of Example 257, Methods A and B, but substituting the compounds indicated in Column I below for N-benzyl-N-(2'-nitro-5'-chlorophenyl)-malonamic acid ethyl ester in Example 257, Methods A and B, the compounds indicated in Column II are obtained.

| I | II |
|---|---|
| 258. N-benzyl-N-[2'-nitro-5'-(trifluoromethyl)phenyl] malonamic acid ethyl ester | N-benzyl-[2'-amino-5'-(trifluoromethyl)phenyl] malonamic acid ethyl ester |
| 259. N-benzyl-N-(2'-nitro-5'-methylphenyl) malonamic acid ethyl ester | N-benzyl-N-(2'-amino-5'-methylphenyl)malonamic acid ethyl ester |
| 260. N-benzyl-N-(2'-nitro-5'-methoxyphenyl) malonamic acid ethyl ester | N-benzyl-N-(2'-amino-5'-methoxyphenyl) malonamic acid ethyl ester |
| 261. N-benzyl-N-(2'-nitro-phenyl)malonamic acid, ethyl ester | N-benzyl-N-(2'-amino-phenyl)malonamic acid, ethyl ester |
| 262. N-benzyl-N-(2'-nitro-4'-chlorophenyl) malonamic acid, ethyl ester | N-benzyl-N-(2'-amino-4'-chlorophenyl) malonamic acid, ethyl ester |
| 263. N-(4-methoxybenzyl)-N-2'-nitro-5'-chlorophenyl)malonamic acid ethyl ester | N-(4-methoxybenzyl)-N-(2'-amino-5'-chlorophenyl)malonamic acid ethyl ester |
| 264. N-(4-methoxybenzyl)-N-[2'-nitro-5'-(trifluoromethyl)phenyl]malonamic acid, ethyl ester | N-(4-methoxybenzyl)-N-[2'-amino-5'-(trifluoromethyl)phenyl]malonamic acid, ethyl ester |
| 265. N-benzyl-N-(2'-nitro-5'-chlorophenyl)malonamic acid methyl ester | N-benzyl-N-(2'-amino-5'-chlorophenyl)malonamic acid methyl ester |
| 266. N-benzyl-N-(2'-nitro-5'-chlorophenyl)malonamic acid butyl ester | N-benzyl-N-(2'-amino-5'-chlorophenyl)malonamic acid butyl ester |
| 267. N-benzyl-N-(2'-nitro-5'-chlorophenyl)malonamic acid phenyl ester | N-benzyl-N-(2'-amino-5'-chlorophenyl)malonamic acid phenyl ester |
| 268. N-benzyl-N-(2'-nitro-5'-chlorophenyl)malonamic acid (p-methyl-phenyl)ester | N-benzyl-N-(2'-amino-5'-chlorophenyl)malonamic acid (p-methylphenyl) ester |

EXAMPLES 269–279

Following the procedure of Example 140, Methods B and D, but substituting the compounds indicated in Column I below for N-benzyl-N-(2'-amino-5'-chlorophenyl) malonamic acid, ethyl ester in Example 140, Methods B and D, the compounds indicated in Column II are obtained.

| | |
|---|---|
| 269. N-benzyl-N-[2'-amino-5'-(trifluoromethyl)- | 7-(trifluoromethyl)-5-benzyl-1H-1,5-benzodia- |

| | |
|---|---|
| phenyl]malonamic acid ethyl ester | zepine-2,4-dione |
| 270. N-benzyl-N-(2'-amino-5'-methylphenyl)malonamic acid ethyl ester | 7-methyl-5-benzyl-1H-1,5-benzodiazepine-2,4-dione |
| 271. N-benzyl-N-(2'-amino-5'-methoxyphenyl)malonamic acid ethyl ester | 7-methoxy-5-benzyl-1H-1,5-benzodiazepine-2,4-dione |
| 272. N-benzyl-N-(2'-aminophenyl)malonamic acid ethyl ester | 5-benzyl-1H-1,5-benzodiazepine-2,4-dione |
| 273. N-benzyl-N-(2'-amino-4'-chlorophenyl)malonamic acid, ethyl ester | 8-chloro-5-benzyl-1H-1,5-benzodiazepine-2,4-dione |
| 274. N-(4-methoxybenzyl)-N-(2'-amino-5'-chlorophenyl)malonamic acid ethyl ester | 7-chloro-5-(p-methoxybenzyl-1H,1,5-benzodiazepine-2,4-dione |
| 275. N-(4-methoxybenzyl)-N-[2'-amino-5'-(trifluoromethyl)phenyl]malonamic acid, ethyl ester | 7-(trifluoromethyl)-5-(p-methoxybenzyl)-1H-1,5-benzodiazepine-2,4-dione |
| 276. N-benzyl-N-(2'-amino-5'-chlorophenyl)malonamic acid methyl ester | 7-chloro-5-benzyl-1H-1,5-benzodiazepine-2,4-dione |
| 277. N-benzyl-N-(2'-amino-5'-chlorophenyl)malonamic acid butyl ester | 7-chloro-5-benzyl-1H-1,5-benzodiazepine-2,4-dione |
| 278. N-benzyl-N-(2'-amino-5'-chlorophenyl)malonamic acid phenyl ester | 7-chloro-5-benzyl-1H-1,5-benzodiazepine-2,4-dione |
| 279. N-benzyl-N-(2'-amino-5'-chlorophenyl)malonamic acid (p-methylphenyl)ester | 7-chloro-5-benzyl-1H-1,5-benzodiazepine-2,4-dione |

EXAMPLE 280

2,7-Dichloro-5-phenyl-3H-1,5-benzodiazepin-4-one

Method A 28.6 g of 7-chloro-5-phenyl-1H-1,5-benzodiazepine-2,4-dione and 20.8 g of phosphorus pentachloride in 1000 ml of benzene is stirred for 10 hours, then refluxed for 3 hours. The reaction is evaporated, azeotroped with benzene and the solvent evaporated. The residue is stirred with carbon tetrachloride and the title compound filtered off and dried.

Method B

To 28.6 g of 7-chloro-5-phenyl-1H-1,5-benzodiazepine-2,4-dione and 24.2 g of dimethylaniline in 200 ml of benzene is added 10.2 g of phosphorous oxychloride. The reaction mixture is refluxed for 14 hours under argon, cooled to 7° C., diluted with 100 ml of cold water and stirred for 0.25 hour. The organic layer is separated, washed with 100 ml of cold water, dried and evaporated. The residue is stirred with 50 ml of carbon tetrachloride and the title compound is filtered off and dried.

EXAMPLE 281

Acetic acid 2-(7-chloro-5-phenyl-3H-1,5-benzodiazepin-4-one-2-yl)hydrazide

Method A 3.0 g of 7-chloro-5-phenyl-1H-1,5-benzodiazepin-4-one-2-thione and 1.8 g of acetic acid hydrazide in 100 ml ethanol is refluxed for 24 hours. During this time a slow stream of nitrogen is bubbled through the reaction mixture. The mixture is evaporated, the residue taken up in methylene chloride, washed with water, dried and the solvent evaporated. The residue is chromatographed on 10–1000μ silica gel plates (20×20 cm) with acetone-methanol (9:1) eluant. The band containing the product is removed and stirred with acetone-methanol (4:1). The silica gel is filtered off and the filtrate evaporated to give the title compound.

Method B 3.0 g of 2-hydrazino-7-chloro-5-phenyl-3H-1,5-benzodiazepin-4-one and 1.4 g of ethyl 1-acetoxyformate in 50 ml tetrahydrofuran containing one drop of N-methylmorpholine is stirred at room temperature for 24 hours. The reaction mixture is evaporated to give the title compound. Further purification is accomplished, if necessary, by chromatography as described in Example 281, Method A.

EXAMPLE 282

2-Hydrazino-7-chloro-5-phenyl-3H-1,5-benzodiazepin-4-one

Method A 3.8 g of 2-[2-(t-butoxycarbonyl)hydrazino]-7-chloro-5-phenyl-3H-1,5-benzodiazepin-4-one and 1.78 g of hydrogen bromide in 200 ml methylene chloride is stirred for 2 hours. The reaction mixture is washed with aqueous sodium bicarbonate, water, dried and evaporated. The product is stirred with carbon tetrachloride and the title compound is filtered off and dried.

Method B 4.32 g of 2-[2-(benzyloxycarbonyl)hydrazino]-7-chloro-5-phenyl-3H-1,5-benzodiazepin-4-one in 400 ml 1,2-dimethoxy-ethane containing 0.4 g of 10% palladium-on-carbon is hydrogenated at 40 p.s.i. hydrogen pressure until 0.01 moles of hydrogen are absorbed. The reaction is filtered, the filtrate evaporated at room temperature and the residue stirred with carbon tetrachloride to give the title compound.

EXAMPLE 283

2-[2-(t-butoxycarbonyl)hydrazino]-7-chloro-5-phenyl-3H-1,5-benzodiazepin-4-one 3.16 g of 2-(methylthio)-7-chloro-5-phenyl-3H-1,5-benzodiazepin-4-one and 1.41 g of t-butylcarbazate in 60 ml of dimethyl formamide are refluxed for 20 hours while a slow stream of nitrogen is bubbled through the reaction. The reaction is worked up as described in Example 29, Method A, to give the title compound.

EXAMPLE 284

2-[2-(Benzyloxycarbonyl)hydrazino]-7-chloro-5-phenyl-3H-1,5-benzodiazepin-4-one

Following the procedure of Example 283, but substituting benzylcarbazate for t-butylcarbazate in Example 283, the title compound is obtained.

EXAMPLE 285

7-Amino-5-phenyl-1H-1,5-benzodiazepine-2,4-dione 29.7 g of 7-nitro-5-phenyl-1H-1,5-benzodiazepine-2,4-dione in 200 ml ethanol containing 1.0 g of Raney nickel is hydrogenated at room temperature at an initial hydrogen pressure of 50 p.s.i. The reaction is stopped after 0.3 moles of hydrogen has been absorbed. The reaction mixture is filtered and the filtrate evaporated to give 7-amino-5-phenyl-3H-1,5-benzodiazepine-2,4-dione.

EXAMPLE 286

7-Diazonium-5-phenyl-1H-1,5-benzodiazepin-4-one, sulfate 20 g of 7-amino-5-phenyl-1H-1,5-benzodiazepine-2,4-dione in 100 ml of acetic acid is added to a solution of 7.62 g of nitrosylsulfuric acid in 10 ml of acetic acid at 0° C. After 30 minutes, 100 ml of ether is added, with stirring and cooling, and the precipitated diazonium sulfate is filtered off and dried.

EXAMPLE 287

7-(Methylthio)-5-phenyl-1H-1,5-benzodiazepine-2,4-dione 3.76 g of 7-diazonium-5-phenyl-1H-1,5-benzodiazepine-2,4-dione sulfate is added portionwise with stirring under a dry-ice condenser, to a solution of 2.58 g of potassium methyl mercaptide in 100 ml of methyl mercaptan. The reaction is gently refluxed for 24 hours. The reaction is evaporated; the residue diluted with 200 ml of methylene chloride, washed with a solution of 1.35 g acetic acid in 100 ml water, dried and evaporated to give the title compound. The product may be further purified by chromatography on silica gel (e.g. 20–1000μ, 20×20 cm plates) using chloroform-ethyl acetate (6:4) as eluting solvent. The band containing the title compound is removed, stirred with EtOAc-MeOH (9:1) and the silica gel is filtered off. The filtrate is evaporated to give the title compound.

EXAMPLE 288

1-Methyl-8-(methylsulfinyl)-6-phenyl-4H-s-triazolo[4,3-a][1,5]benzodiazepin-5-one 3.36 g of 1-methyl-8-(methylthio)-6-phenyl-4H-s-triazolo[4,3-a][1,5]benzodiazepin-5-one and 2.14 g of sodium metaperiodate in 500 ml methanol is stirred at +5° C. for 24 hours. The reaction is evaporated; the residue dissolved in methylene chloride, washed with water, dried and concentrated. The concentrate is chromatographed on silica gel (20–1000μ plates, 20×20 cm) using acetone-methanol (9:1) as eluting solvent. The band containing the product is removed, stirred with acetone-methanol (4:1) and the silica gel filtered off. The filtrate is evaporated to give the title compound.

EXAMPLE 289

1-Methyl-8-amino-6-phenyl-4H-s-triazolo[4,3-a][1,5]benzodiazepin-5-one 33.5 g of 1-methyl-8-nitro-6-phenyl-4H-s-triazolo[4,3-a][1,5]benzodiazepin-5-one in 100 ml of ethanol containing 2.0 g of Raney nickel is hydrogenated at room temperature at an initial hydrogen pressure of 50 p.s.i. The reaction is stopped when 0.3 moles of hydrogen has been absorbed; the suspension is filtered and the filtrate evaporated to give the title compound.

EXAMPLE 290

1-Methyl-8-acetamido-6-phenyl-4H-s-triazolo[4,3-a][1,5]benzodiazepin-5-one 3.47 g of 1-methyl-8-amino-6-phenyl-4H-s-triazolo[4,3-a][1,5]benzodiazepin-5-one and 1.02 g of acetic anhydride in 50 ml pyridine is stirred for 12 hours then refluxed for 30 minutes. The reaction is evaporated; the residue is taken up in chloroform, washed with dilute aqueous sodium bicarbonate, with water and dried. The solvent is evaporated to give the title compound.

EXAMPLE 291

4-Hydroxy-1-methyl-8-chloro-6-phenyl-4H-s-triazolo[4,3-a][1,5]benzodiazepin-5-one 44.6 g of 4-(benzyloxy)-1-methyl-8-chloro-6-phenyl-4H-s-triazolo[4,3-a][1,5]benzodiazepin-5-one in 400 ml of ethanol containing 2.0 g of Raney nickel is hydrogenated at an initial hydrogen pressure of 40 p.s.i. After 0.1 mole of hydrogen has been absorbed, the reaction is stopped, filtered and the solvent evaporated. The residue is triturated in ether and the title compound filtered off and dried.

EXAMPLES 292–296

Following the procedure of Example 124, but substituting the compounds indicated in column I below for diethylamine in example 124, the compounds in column II are obtained.

| I | II |
|---|---|
| 292. 4-phenylpiperidine | 1-(4-phenylpiperidinomethyl)-8-chloro-6-phenyl-4H-s-triazolo-[4,3-a][1,5]benzodiazepin-5-one |
| 293. N-methylpiperazine | 1-(4-methylpiperazinomethyl)-8-chloro-6-phenyl-4H-s-triazolo[4,3-a][1,5]benzodiazepin-5-one |
| 294. N-(2-methoxyphenyl)-piperazine | 1-[4-(2-methoxyphenyl)piperazinomethyl]-8-chloro-6-phenyl-4H-s-triazolo[4,3-a][1,5]benzodiazepin-5-one |
| 295. silver nitrite | 1-(nitromethyl)-8-chloro-6-phenyl-4H-s-triazolo[4,3-a][1,5]benzodiazepin-5-one |
| 296. N-(t-butoxycarbonyl)-piperazine | 1-[4-(t-butoxycarbony)-piperazinomethyl]-8-chloro-6-phenyl-4H-s-triazolo[4,3-a][1,5]-benzodiazepin-5-one |

EXAMPLE 297

1-Piperazinomethyl-8-chloro-6-phenyl-4H-s-triazolo[4,3-a][1,5]benzodiazepin-5-one 2 g. of 1-[4-(t-butoxycarbonyl)-piperazinomethyl]-8-chloro-6-phenyl-4H-s-triazolo[4,3-a][1,5]benzodiazepin-5-one in 50 ml of trifluoroacetic acid is stirred for 2 hours. The reaction mixture is evaporated and the residue partitioned between methylene chloride and aqueous sodium bicarbonate. The organic phase is washed with water, dried and evaporated to give the title compound.

EXAMPLE 298

4-(3,4,5-trimethoxybenzoyloxy)-8-chloro-6-phenyl-4H-s-triazolo[4,3-a][1,5]benzodiazepin-5-one Following the procedure of example 281, method B, but substituting ethyl 1-(3,4,5-trimethoxybenzoyloxy)-formate for ethyl 1-acetoxyformate and 4-hydroxy-8-chloro-6-phenyl-4H-s-triazolo[4,3-a][1,5]benzodiazepin-5-one for 2-hydrazino-7-chloro-5-phenyl-3H-1,5-benzodiazepin-4-one in example 281, method B, the title compound is obtained.

EXAMPLE 299

1-Methyl-8-chloro-6-(2',4'-dichlorophenyl)-4H-s-triazolo-[4,3-a][1,5]benzodiazepin-5-one Part A 20 g of 2',4',5-trichloro-2-nitrodiphenylamine in 100 ml of methanol containing 0.2 g of Raney nickel is hydrogenated at an initial hydrogen pressure of 7 atm. until three molar equivalents of hydrogen is consumed. The suspension is filtered and the filtrate evaporated to give the 2',4',5-trichloro-2-aminodiphenylamine.

Part B

Following the procedure of example 140, method A, but substituting the above produced 2',4',5-trichloro-2-aminodiphenylamine for 2-benzylamino-4-chloro-aniline in example 140, method A, gives 7-chloro-(2',4'-dichlorophenyl)-1H-1,5-benzodiazepin-2,4-dione.

Part C

Following the procedure of example 1 but substituting the above produced 7-chloro-5-(2',4'-dichlorophenyl)-1H-1,5-benzodiazepin-2,4-dione for 7-chloro-5-phenyl-1H-1,5-benzodiazepine-2,4-dione in example 1, gives 7-chloro-5-(2',4'-dichlorophenyl)-1H-1,5-benzodiazepin-4-one-2-thione.

Part D

Following the procedure of example 29, method A, but substituting the above produced 7-chloro-5-(2',4'-dichlorophenyl)-1H-1,5-benzodiazepin-4-one-2-thione for 7-chloro-5-phenyl-1H-1,5-benzodiazepin-4-one-2-thione in example 29, method A, gives the title compound of formula 1.

EXAMPLES 300–318

Following the procedure of parts A to D of the foregoing example but employing as starting materials the substituted compound of formula 15 wherein m is zero wherein the substituents and the position they occupy are indicated below:

| Example No. | 3 | 4 | 5 | 6 | 2' | 3' | 4' | 5' | 6' |
|---|---|---|---|---|---|---|---|---|---|
| 300. |  | Cl | Cl |  |  |  |  |  |  |
| 301. | Cl |  |  |  |  |  |  |  |  |
| 302. |  | Cl |  |  |  |  |  | $CH_3SO_2$ |  |
| 303. |  | $CF_3$ |  |  | Cl |  |  |  | $CF_3$ |
| 304. |  |  | Cl |  |  | $CH_3$ | $CH_3$ |  |  |
| 305. |  |  | Cl |  |  | $CH_3$ |  | Cl |  |
| 306. |  |  | $CH_3S$ |  |  |  |  | Cl |  |
| 307. |  |  | Cl |  | Cl |  |  | $CH_3$ |  |
| 308. |  | Cl |  | Cl |  |  |  |  |  |
| 309. |  | $CH_3O$ | $CH_3O$ |  |  |  |  |  |  |
| 310. |  | Cl | Cl |  |  |  | Cl |  |  |
| 311. |  | Cl |  |  | $OCH_3$ |  |  | $OCH_3$ |  |
| 312. |  |  |  | Cl |  |  |  |  |  |
| 313. |  |  |  |  | Cl | Cl |  |  |  |
| 314. | $CH_3O$ |  |  |  | $CH_3O$ |  |  |  |  |
| 315. |  | Cl | $CH_3$ |  |  |  |  |  |  |
| 316. |  | $CH_3SO_2$ |  |  |  |  |  |  |  |
| 317. |  | Cl |  |  |  |  | $CH_3S$ |  |  |
| 318. |  | Cl |  |  |  |  | $CH_3SO_2$ |  |  |
| 319. |  | Cl |  | F |  |  |  |  |  | there is obtained the correspondingly substituted compound of formula I wherein the substituents and the position they occupy are indicated below:

| Example No. | 7 | 8 | 9 | 10 | 2' | 3' | 4' | 5' | 6' |
|---|---|---|---|---|---|---|---|---|---|
| 300. |  | Cl | Cl |  |  |  |  |  |  |
| 301. |  |  |  | Cl |  |  |  |  |  |
| 302. |  | Cl |  |  |  |  |  | $CH_3SO_2$ |  |
| 303. |  | $CF_3$ |  |  | Cl |  |  |  | $CF_3$ |
| 304. |  | Cl |  |  |  | $CH_3$ | $CH_3$ |  |  |
| 305. |  | Cl |  |  |  | $CH_3$ |  | Cl |  |
| 306. |  | $CH_3S$ |  |  |  |  |  | Cl |  |
| 307. |  | Cl |  |  | Cl |  |  | $CH_3$ |  |
| 308. | Cl |  | Cl |  |  |  |  |  |  |
| 309. |  | $CH_3O$ | $CH_3O$ |  |  |  |  |  |  |
| 310. |  | Cl | Cl |  |  |  | Cl |  |  |
| 311. |  |  | Cl |  | $OCH_3$ |  |  | $OCH_3$ |  |
| 312. | Cl |  |  |  |  |  |  |  |  |
| 313. |  |  |  |  | Cl | Cl |  |  |  |
| 314. | $OCH_3$ |  |  |  | $OCH_3$ |  |  |  |  |
| 315. |  | $CH_3$ | Cl |  |  |  |  |  |  |
| 316. |  |  | $CH_3SO_2$ |  |  |  |  |  |  |
| 317. |  | Cl |  |  |  |  |  | $SCH_3$ |  |
| 318. |  | Cl |  |  | $CH_3SO_2$ |  |  |  |  |
| 319. |  | Cl |  |  | F |  |  |  | F |

EXAMPLE 320

1-Methyl-8-(methylsulfonyl)-6-phenyl-4H-s-triazolo[4,3-a][1,5]benzodiazepin-5-one Following the procedure of example 288, but using 4.14 g instead of 2.14 g of sodium metaperiodate, the title compound is obtained.

EXAMPLE 321

4-Chloro-2',6'-difluoro-2-nitrophenylamine 19.1 g of 2,4-dichloronitrobenzene and 126.0 g of 2,6-difluoroaniline and 16.4 g of sodium acetate are refluxed for 24 hours. After cooling, the reaction is poured into excess dilute hydrochloric acid, extracted with ether and the ether is then dried and evaporated. The residue from the ether phase is chromatographed on neutral alumina with hexane-ether (9:1). The eluant is evaporated. The title compound is purified by recrystallization from ethanol.

EXAMPLE 322

1-Methyl-8-chloro-6-(5'-chloro-2'-nitrophenyl)-4H-s-triazolo[4,3-a][1,5]benzodiazepin-5-one Following the procedure of parts B through D of example 299, but substituting 2-amino-5'-chloro-2'-nitrodiphenylamine for 2',4',5-trichloro-2-aminodiphenylamine in part B, the title compound is obtained.

EXAMPLE 323

1-Ethoxymethyl-8-chloro-6-phenyl-4H-s-triazolo[4,3-a][1,5]benzodiazepin-5-one

Following the procedure of example 124, but substituting sodium ethoxide and ethanol for diethylamine in example 124, the title compound is obtained.

EXAMPLE 324

4-(2-Dimethylaminoethyl)-1-methyl-8-chloro-6-phenyl-4H-s-triazolo[4,3-a][1,5]benzodiazepin-5-one 37.0 g of 1-methyl-8-chloro-6-phenyl-4H-s-triazolo[4,3-a][1,5]benzodiazepin-5-one and 7.8 g of a 50 percent sodium hydride mineral oil dispersion in 400 ml of dry 1,2-dimethoxyethane are stirred for 2 hours. A solution of 13.7 g of 2-dimethylaminoethyl bromide in 40 ml of dry 1,2-dimethoxyethane is added and the whole is stirred for 18 hours. The solvent is evaporated and the residue is partitioned between methylene chloride and water. The organic phase is washed with water, dried and evaporated to give the title compound.

EXAMPLES 325–338

Following the procedure of example 324 but substituting the compounds indicated in column I below for 2-dimethylaminoethyl bromide in example 324, the compounds indicated in column II are obtained:

| | I | II |
|---|---|---|
| 325. | 3-dimethylaminopropyl chloride | 4-(3-dimethylaminopropyl)-1-methyl-8-chloro-6-phenyl-4H-s-triazolo[4,3-a][1,5-]benzodiazepin-5-one |
| 326. | 2-pyrrolidinoethyl chloride | 4-(2-pyrrolidinoethyl)-1-methyl-8-chloro-6-phenyl-4H-s-triazolo[4,3-a][1,5]benzodiazepin-5-one |
| 327. | 2-diethylaminoethyl bromide | 4-(2-diethylaminoethyl)-1-methyl-8-chloro-6-phenyl-4H-s-triazolo[4,3-a][1,5]benzodiazepin-5-one |
| 328. | 2-morpholinoethyl chloride | 4-(2-morpholinoethyl)-1-methyl-8-chloro-6-phenyl-4H-s-triazolo[4,3-a][1,5]benzodiazepin-5-one |
| 329. | 2-piperidonethyl chloride | 4-(2-piperidinoethyl)-1-methyl-8-chloro-6-phenyl-4H-s-triazolo[4,3-a][1,5]benzodiazepin-5-one |
| 330. | 2-(4-phenylpiperidino)ethyl chloride | 4-[2-(4-phenylpiperidino)ethyl]-1-methyl-8-chloro-6-phenyl-4H-s-triazolo[4,3-a][1,5]benzodiazepin-5-one |
| 331. | 2-piperazinoethyl chloride | 4-(2-piperazinoethyl)-1-methyl-8-chloro-6-phenyl-4H-s-triazolo[4,3-a][1,5]benzodiazepin-5-one |
| 332. | 2-(4-methylpiperazino-ethyl chloride | 4-[2-(4-methylpiperazino)ethyl]-1-methyl-8-chloro-6-phenyl-$H-s-triazolo[4,3-a][1,5]benzodiazepin-5-one |
| 333. | 2-(4-phenylpiperazino)ethyl chloride | 4-[2-(4-phenylpiperazino)ethyl]-1-methyl-8-chloro-6-phenyl-4H-s-triazolo[4,3-a]1,5]benzodiazepin-5-one |
| 334. | 3-[4-(2-methoxyphenyl)piperazino]propyl chloride [1,5]benzodiazepin-5-one | 4-[3-[4-(2-methoxyphenyl)piperazino]propyl]-1-methyl-8-chloro-6-phenyl-4H-s-triazolo[4,3-a]- |
| 335. | 3-piperidinopropyl chloride | 4-(3-piperidinopropyl)-1-methyl-8-chloro-6-phenyl-4H-s-triazolo-[4,3-a][1,5]benzodiazepin-5-one |
| 336. | 3-(4-methylpiperazino)propyl chloride | 4-[3-(4-methylpiperazino)propyl]-1-methyl-8-chloro-6-phenyl-4H-s-triazolo[4,3-a][1,5-]benzodiazepin-5-one |
| 337. | 2-(N-benzyl-N-methylamino)ethyl chloride | 4-[2-(N-benzyl-N-methylamino)ethyl]-1-methyl-8-chloro-6-phenyl-4H-s-triazolo[4,3-a][1,5]benzodiazepin-5-one |
| 338. | 3-[(t-butoxycarbonyl)amino]propyl chloride benzodiazepin-5-one | 4-[3-[(t-butoxycarbonyl)amino]propyl]-1-methyl-8-chloro-6-phenyl-4H-s-triazolo[4,3-a][1,5]- |

EXAMPLE 339

4-(2-Methylaminoethyl)-1-methyl-8-chloro-6-phenyl-4-H-s-triazolo[4,3-a][1,5]benzodiazepin-5-one 4 g of 4-[2-(N-benzyl-N-methylamino)ethyl]-1-methyl-8-chloro-6-phenyl-4H-s-triazolo[4,3-a][1,5]benzodiazepin-5-one in 100 ml of ethanol containing 0.4 g of Raney nickel is hydrogenated at 50 p.s.i. hydrogen pressure until 0.0085 moles of hydrogen is absorbed. The suspension is filtered and the filtrate is evaporated. The residue is triturated with a small amount of cold ether and the title compound is filtered off and dried.

EXAMPLE 340

4-(3-aminopropyl)-1-methyl-8-chloro-6-phenyl-4H-s-triazolo[4,3-a][1,5]benzodiazepin-5-one 2.5 g of 4-[2-(N-t-butoxycarbonylamino)propyl]-1-methyl-8-chloro-6-phenyl-4H-s-triazolo[4,3-a][1,5]benzodiazepin-5-one in 50 ml of trifluoroacetic acid is stirred at room temperature for 2 hours. The reaction is evaporated and the residue is stirred with a solution of 1.9 g of sodium bicarbonate in 400 ml of methanol-water (10:1). After 3 hours the reaction is evaporated and the residue is partitioned between methylene chloride and water. The methylene chloride is washed with water, dried and evaporated to give the title compound.

EXAMPLES 341–343

Following the procedure of example 29, Method A, but substituting the compounds indicated in column I below for acetic acid hydrazide in example 29, Method A, the compounds indicated in column II are obtained.

| | I | II |
|---|---|---|
| 341. | picolinic acid hydrazide | 1-(2-pyridyl)-8-chloro-6-phenyl-4H-s-triazolo[4,3-a][1,5]benzo- |

| | I | II |
|---|---|---|
| 342. | nicotinic acid hydrazide | 1-(3-pyridyl)-8-chloro-6-phenyl-4H-s-triazolo[4,3-a][1,5]benzodiazepin-5-one |
| 343. | isonicotinic acid hydrazide | 1-(4-pyridyl)-8-chloro-6-phenyl-4H-s-triazolo[4,3-a][1,5]benzodiazepin-5-one |
| 343. | m-(trifluoromethyl) benzoic acid hydrazide | 1-[3-(trifluoromethyl)phenyl]-8-chloro-6-phenyl-4H-s-triazolo-[4,3-a][1,5]benzodiazepin-5-one |
| 344. | o-chlorobenzoic acid hydrazide | 1-(2-chlorophenyl)-8-chloro-6-phenyl-4H-s-triazolo[4,3-a][1,5]-benzodiazepin-5-one |
| 345. | p-methylbenzoic acid hydrazide | 1-(4-methylphenyl)-8-chloro-6-phenyl-4H-s-triazolo[4,3-a][1,5]-benzodiazepin-5-one |
| 346. | m-methoxybenzoic acid hydrazide | 1-(3-methoxyphenyl)-8-chloro-6-phenyl-4H-s-triazolo[4,3-a][1,5]-benzodiazepin-5-one |
| 347. | m-nitrobenzoic acid hydrazide | 1-(3-nitrophenyl)-8-chloro-6-phenyl-4H-s-triazolo[4,3-a][1,5]-benzodiazepin-5-one |
| 348. | p-acetamidobenzoic acid hydrazide | 1-(4-acetamidophenyl)-8-chloro-6-phenyl-4H-s-triazolo[4,3-a][1,5]-benzodiazepin-5-one |
| 349. | o-(methylthio) benzoic | 1-[2-(methylthio)phenyl]-8-chloro-6-phenyl-4H-s-triazolo[4,3-a][1,5]-benzodiazepin-5-one |
| 350. | p-(methylsulfonyl)-benzoic acid hydrazide | 1-[4-(methylsulfonyl)phenyl]-8-chloro-6-phenyl-4H-s-triazolo-[4,3-a][1,5]benzodiazepin-5-one |

EXAMPLE 351

A group of experimental animals composed of rats, mice and monkeys are orally administered 1-methyl-8-chloro-6-phenyl-4H-s-triazolo-[4,3-a][1,5]benzodiazepin-5-one. The compound is administered at the following dosage levels: rats, 3.1 mg/kg; mice, 1 mg/kg; monkeys, 2.5 mg/kg. Ataxia is produced in all of the animals of the test group at the dosage levels indicated.

EXAMPLE 352

A group of rats is orally administered 1-methyl-8-chloro-6-phenyl-4H-s-triazolo[4,3-a][1,5]benzodiazepin-5-one. The group is then subjected to the conflict test procedure described by Vogel et al., Psychopharmacologist, b 21, 1 (1970). A tranquilizing effect is produced in all of the test animals.

EXAMPLE 353

A group of mice is orally administered 1-methyl-8-chloro-6-phenyl-4H-s-triazolo[4,3-a][1,5]benzodiazepin-5-one at a dosage level of 12 mg/kg. At this dosage level the convulsant effect of 135 mg of subcutaneously administered pentylenetetrazole is antagonized in 50% of the animals.

EXAMPLE 354

In another test, the same group of mice is orally administered 26 mg/kg of the foregoing compound. This dosage level antagonizes the convulsant effect of 75 mg of intravenously administered strychnine in 50% of the test animals.

EXAMPLE 355

A group of mice are orally administered 30 mg/kg of 1-methyl-8-chloro-6-phenyl-4H-s-triazolo[4,3-a][1,5]benzodiazepin-5-one. Food consumption is increased in the test animals by 100% compared to a group of control animals.

EXAMPLE 356

Preparation of capsule formulation

| Ingredient | Milligrams per Capsule |
|---|---|
| 1-Methyl-8-chloro-6-phenyl-4H-s-triazolo[4,3-a][1,5]benzodiazepin-5-one | 400 |
| Starch | 80 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 357

Preparation of tablet formulation

| Ingredient | Milligrams per Tablet |
|---|---|
| 1-Methyl-8-chloro-6-phenyl-4H-s-triazolo[4,3-a][1,5]benzodiazepin-5-one | 300 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 300 milligrams of active ingredient.

EXAMPLE 358

Preparation of oral syrup formulation

| Ingredient | Amount | |
|---|---|---|
| 1-Methyl-8-chloro-6-phenyl-4H-s-triazolo[4,3-a][1,5]benzodiazepin-5-one | 500 | mg. |
| Sorbitol solution (70% N.F.) | 40 | ml. |
| Sodium benzoate | 150 | mg |
| Sucaryl | 90 | mg. |
| Saccharin | 10 | mg. |
| Red Dye (F.D. & Co. No. 2) | 10 | mg. |
| Cherry flavor | 50 | mg. |
| Distilled water   qs to | 100 | ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A method for promoting growth rate or feed efficiency in livestock which comprises administering to said livestock a growth promoting amount of a compound of the structure

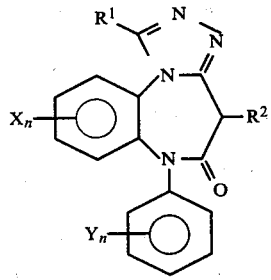

wherein
R$^1$ is phenyl; X-substituted phenyl wherein X is as defined below; 2-, 3- or 4-pyridyl, cycloalkyl of 3-5 carbons;
R$^2$ is H; alkyl of 1-4 carbons optionally substituted by amino, mono-lower alkyl, di-lower alkyl amino, cyclic imines of formula

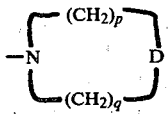

where D is methylene, oxygen or N-R$^{10}$ and where p and q are the same or different and are the integers 1, 2, and 3 provided that p+q is at least 1; hydroxy; alkoxy of 1-6 carbons or

wherein

is an acyl group capable of removal and replacement by hydrogen or alkyl of 1-4 carbons and R$^5$ is alkyl of 1-5 carbons optionally substituted by phenyl or X-substituted phenyl; or R$^5$ is phenyl optionally substituted by 1 or more X-substitutents;

X and Y are the same or different and are hydrogen, F, Cl, Br, trifluoromethyl, alkyl of from 1-6 carbons, alkoxy of from 1-6 carbons, nitro, cyano, amino, alkanoylamino of 1-4 carbons, alkylthio of 1-6 carbons, alkylsulfinyl of 1-6 carbons or alkyl sulfonyl of 1-6 carbons;

R$^{10}$ is hydrogen, alkyl of 1-4 carbons or phenyl optionally substituted by X, wherein X is as defined above; and n is 0, 1 or 2.

2. The method according to claim 1 where in in said compound R$^1$ is cycloalkyl of 3-5 carbons.

3. The method according to claim 1 where in said compound R$^2$ is hydrogen, alkyl of from 1-4 carbon atoms or hydroxy.

4. The method according to claim 1 wherein in said compound R$^1$ is phenyl, or pyridyl, R$^2$ is hydrogen, X$_n$ is hydrogen, chloro, trifluoromethyl, thiomethyl or nitro, each of the foregoing being in the 8-position and Y$_n$ is fluoro or chloro in the 2'-position, or Y$_n$ is difluoro in the 2'- and 6'-positions.

5. The method according to claim 1 where in said compound R$^2$ is hydrogen, methyl, dimethylaminomethyl or diethylaminomethyl.

6. The method according to claim 5 where in said compound R$^1$ is phenyl, or pyridyl, R$^2$ is hydrogen, methyl, dimethylaminomethyl, or diethylaminomethyl, X$_n$ is chloro in the 8-position and Y$_n$ is fluoro or chloro in the 2'-position or difluoro in the 2'-position and 6'-positions.

7. The method according to claim 6 where in said compound R$^2$ is hydrogen or methyl, X$_n$ is chloro in the 8-position and Y$_n$ is chloro in the 2'-position.

* * * * *

UNITED STATES PATENT AND TRADEMARK OFFICE
CERTIFICATE OF CORRECTION

PATENT NO. : 4,213,982

DATED : July 22, 1980

INVENTOR(S) : B. Richard Vogt

It is certified that error appears in the above-identified patent and that said Letters Patent are hereby corrected as shown below:

Column 15, line 39, "referably" should read --preferably--.
Column 18, line 58, "agents" should read --agent--.
Column 30, line 23, after "4H-" insert -- s- --.
Column 30, line 51, "4acetoxy" should read --4-acetoxy--.
Column 37, Example 229, Column II, line 2, after "4H-" insert -- s- --.
Column 37, Example 230, Column II, line 2, after "4H-" insert -- s- --.
Column 39, Example 246, Column I, line 2, "trifluoromethyl" should read --(trifluoromethyl)--; and Column II, line 2, after "(trifluoromethyl)" insert --phenyl--.
Column 39, Example 250, Column 1, line 1, "2' " should read --2--.
Column 39, Example 253, Column I, line 1, before "chloroformyl)" insert --(--.
Column 40, Example 258, Column II, line 1, after "N-benzyl-" insert -- N- --.
Column 41, Example 278, Column I, line 2, after "malona" insert a hyphen.
Column 46, Example 319, Column 6', insert --F--.
Column 48, Example 331, delete "zepin-5-one" from Column I and insert as the last line in Column II.

UNITED STATES PATENT AND TRADEMARK OFFICE
CERTIFICATE OF CORRECTION

PATENT NO. : 4,213,982　　　　　　　　　　　Page 2 of 2

DATED : July 22, 1980

INVENTOR(S) : B. Richard Vogt

It is certified that error appears in the above-identified patent and that said Letters Patent are hereby corrected as shown below:

Column 48, Example 334, delete "[1,5]benzodiazepin-5-one" from Column I and insert as the last two lines in Column II.

Column 48, Example 338, delete "benzodiazepin-5-one" from Column I and insert as the last line in Column II.

Column 49, line 46, delete the "b" before "21".

Signed and Sealed this

Eighteenth Day of November 1980

[SEAL]

Attest:

SIDNEY A. DIAMOND

Attesting Officer　　　　Commissioner of Patents and Trademarks